United States Patent
Cao et al.

(10) Patent No.: US 9,239,334 B2
(45) Date of Patent: Jan. 19, 2016

(54) FATTY ACID C16: 1N7-PALMITOLEATE A LIPOKINE AND BIOMARKER FOR METABOLIC STATUS

(75) Inventors: Haiming Cao, Bethesda, MD (US); Gokhan S. Hotamisligil, Wellesley, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 431 days.

(21) Appl. No.: 13/062,527

(22) PCT Filed: Sep. 8, 2009

(86) PCT No.: PCT/US2009/056176
§ 371 (c)(1),
(2), (4) Date: May 23, 2011

(87) PCT Pub. No.: WO2010/028336
PCT Pub. Date: Mar. 11, 2010

(65) Prior Publication Data
US 2011/0213032 A1  Sep. 1, 2011

Related U.S. Application Data

(60) Provisional application No. 61/095,109, filed on Sep. 8, 2008.

(51) Int. Cl.
*A01N 37/00* (2006.01)
*A61K 31/20* (2006.01)
*G01N 33/92* (2006.01)
*A23L 1/30* (2006.01)

(52) U.S. Cl.
CPC .............. *G01N 33/92* (2013.01); *A23L 1/3008* (2013.01); *A61K 31/20* (2013.01); *G01N 2800/04* (2013.01)

(58) Field of Classification Search
USPC ........................................................ 514/560
See application file for complete search history.

(56) References Cited

U.S. PATENT DOCUMENTS

| | | | |
|---|---|---|---|
| 5,198,250 | A | 3/1993 | Brillhart et al. |
| 5,977,175 | A | 11/1999 | Lin |
| 6,461,662 | B2 | 10/2002 | Cain et al. |
| 7,025,984 | B1 | 4/2006 | Jandacek et al. |
| 2004/0106589 | A1 | 6/2004 | Webb et al. |
| 2006/0183797 | A1 | 8/2006 | Cohen et al. |
| 2007/0098808 | A1 | 5/2007 | Sampalis |
| 2009/0202519 | A1 | 8/2009 | Beutler et al. |
| 2009/0215681 | A1 | 8/2009 | Kahn et al. |
| 2009/0239253 | A1 | 9/2009 | Watkins |

OTHER PUBLICATIONS

Mustad et. al. (Metabolism Clinical and Experimental (2006) 55:1365-1374).*
Dimopoulos et. al. (Biochem. J. (2006) 399:473-481).*
Bajaj M., et al., Diabetes 54(11):3148-3153 (Nov. 2005). "Effect of a sustained reduction in plasma free fatty acid concentration on intramuscular long-chain fatty Acyl-CoAs and insulin action in type 2 diabetic patients."
Diakogiannaki E., et al., J Endocrinol. 194(2):283-291 (Aug. 2007). "Mechanisms involved in the cytotoxic and cytoprotective actions of saturated versus monounsaturated long-chain fatty acids in pancreatic beta-cells."
Dimopoulos N. et al., Biochem J. 399(3):473-481 (Nov. 1, 2006). "Differential effects of palmitate and palmitoleate on insulin action and glucose utilization in rat L6 skeletal muscle cells."
Dobrzyn A. et al., J Physiol Pharmacol. 57 Suppl 10:31-42 (Nov. 2006). "Stearoyl-CoA desaturase—a new player in skeletal muscle metabolism regulation."
Fukuchi S., et al., Exp Biol Med (Maywood) 229(6):486-493 (Jun. 2004). "Role of fatty acid composition in the development of metabolic disorders in sucrose-induced obese rats."
Kusunoki M., et al., J Med Invest. 54(3-4):243-247 (Aug. 2007). "Relationship between serum concentrations of saturated fatty acids and unsaturated fatty acids and the homeostasis model insulin resistance index in Japanese patients with type 2 diabetes mellitus."
Maedler K., et al., Diabetes 52(3):726-733 (Mar. 2003). "Monounsaturated fatty acids prevent the deleterious effects of palmitate and high glucose on human pancreatic beta-cell turnover and function."
Okada T., et al., Am J Clin Nutr. 82(4):747-750 (Oct. 2005). "Plasma palmitoleic acid content and obesity in children."
Sauma et al., Nutrition 22(1):60-68 (2005). "PPAR-γ response element activity in intact primary human adipocytes: effects of fatty acids."
Welters, H.J. et al., FEBS Letters, 560(1):103-108 (2004). "Monounsaturated fatty acids protect against L-cell apoptosis induced by saturated fatty acids, serum withdrawal or cytokine ex porere."

* cited by examiner

*Primary Examiner* — Marcos Sznaidman
(74) *Attorney, Agent, or Firm* — Nixon Peabody LLP

(57) ABSTRACT

The present invention provides for a novel lipokine, C16:1n7-palmitoleate, which also serves as a biomarker for metabolic status. More specifically, a low concentration of C16:1n7-palmitoleate in the free fatty acid component of the serum indicates a risk of metabolic disease, and that de novo lipogenesis should be stimulated. Additionally, administering C16:1n7-palmitoleate to a subject (via nutraceutical or other means), positively impacts lipid metabolism.

1 Claim, 28 Drawing Sheets

Plasma fatty acid profiles from mice under high-fat diet

|  | Mean | | | | P-value | |
| --- | --- | --- | --- | --- | --- | --- |
|  | HDK | HWT | RDK | RWT | RDK vs HDK | RWT vs HWT |
| DG16:1n7 | 16.15 | 3.86 | 18.84 | 6.03 | 0.01 | 0.02 |
| FA16:1n7 | 11.10 | 5.73 | 13.82 | 6.26 | 0.20 | 0.79 |
| PC16:1n7 | 4.43 | 2.92 | 5.07 | 2.38 | 0.53 | 0.60 |
| TG16:1n7 | 18.07 | 3.49 | 18.17 | 5.64 | 0.87 | 0.00 |

18s
Forward Primer AGTCCCTGCCCTTTGTACACA
Reverse Primer CGATCCGAGGGCCTCACTA

Beta-actin
Forward Primer GCT GTG CTA TGT TGC TCT AG
Reverse Primer CGC TCG TTG CCA ATA GTG ACC1
Forward Primer CTTCCTGACAAACGAGTCTGG
Reverse Primer CTGCCGAAACATCTCTGGGA FAS
Forward Primer GGAGGTGGTGATAGCCGGTAT
Reverse Primer TGGGTAATCCATAGAGCCCAG SCD-1
Forward Primer TTCTTGCGATACACTCTGGTGC
Reverse Primer CGGGATTGAATGTTCTTGTCGT ELOVL6
Forward Primer GAAAAGCAGTTCAACGAGAACG
Reverse Primer AGATGCCGACCACCAAAGATA Spot 14
Forward Primer ATGCAAGTGCTAACGAAACGC
Reverse Primer CCTGCCATTCCTCCCTTGG DGAT1
Forward Primer TCCGTCCAGGGTGGTAGT
Reverse Primer TGAACAAAGAATCTTGCAGACGA

Figure 22

FATTY ACID C16: 1N7-PALMITOLEATE A LIPOKINE AND BIOMARKER FOR METABOLIC STATUS

FEDERAL FUNDING

This invention was made with U.S. government support under grants DK71507-04 and DK 064360, each awarded by the National Institutes of Health. The U.S. government has certain rights in the invention.

CROSS REFERENCE TO RELATED APPLICATIONS

This application is a 371 National Phase Entry Application of International Application No. PCT/US2009/056176 filed Sep. 8, 2009, which designates the U.S., and which claims the benefit of priority under 35 U.S.C. §119(e) of U.S. Provisional Application Ser. No. 61/095,109, filed Sep. 8, 2008, the contents of which are incorporated herein by reference in their entirety.

FIELD OF THE INVENTION

The present invention relates to molecular biology and cell metabolism. More specifically, the present embodiments provide for a novel lipokines, C16:1n7-palmitoleate, stimulation of adipose de novo fatty acid synthesis, and resistance to metabolic abnormalities.

BACKGROUND

In recent years, the world has seen an alarming increase in metabolic diseases including obesity, insulin resistance, diabetes, fatty liver disease, and atherosclerosis. For example, over twenty million children and adults in the U.S., or 8% of the population, suffer from diabetes. Atherosclerosis is a leading cause of coronary heart disease and stroke, killing more than 600,000 Americans annually: more than 25% of all deaths in the U.S.

Dysregulation of tissue lipid composition or metabolism can lead to disruption of systemic insulin action and glucose metabolism in adipose, muscle, and liver tissues. Recent studies have clearly identified adipose tissue as a critical site for whole body metabolic regulation. A growing body of evidence supports the concept that peptides and hormones produced within the adipose tissue constitute an important component of the endocrine effects of this site on systemic carbohydrate and lipid homeostasis. There have been important advances in the identification of these molecules and characterization of their biological functions. As the major storage site for body lipids, adipose tissue has also been studied intensively in regards to its role in metabolic regulation through lipids. Although equally critical as peptide hormones, this area has been more challenging to reduce into molecular entities and pathways.

There are two prevailing views about the role of adipose tissue lipid metabolism in metabolic syndrome. First, storage of lipids in adipose tissue has been suggested to protect other organs, especially those that are not well equipped for such burden, from exposure to excessive lipids and thereby reducing the risk of lipotoxicity. Second, fatty acids derived from adipose tissue, particular under pathological conditions like obesity, could disrupt the function of peripheral tissues, resulting in muscle insulin resistance or increased triglyceride accumulation in liver. In these models, the principle consideration has often been the total amount of fatty acid exposure at different target tissues.

Serum fatty acids represent a very complex entity, however, and are composed of structures with varying chain lengths and degrees of saturation. The concentration and composition of fatty acids vary significantly under different physiological and pathological conditions, and these changes are not uniform between cell types and tissues. Although it is unlikely that the total fatty acid levels, alone, could be sufficiently informative, there has been some progress in addressing how different compositions of fatty acids in tissues or circulation may affect the metabolic output locally or systemically, but this has been experimentally challenging. Another intractable question has been how to address lipid storing and/or disposing in tissues responding to the dietary fatty acid intake, and how to adjust the composition to modulate metabolic outcomes. Hence, there remains a need for better understanding of the regulation of systemic fatty acid metabolism, and development of further diagnosis and treatment of fatty acid metabolism-related illnesses.

SUMMARY

The present invention relates to new biomarkers to monitor fatty acid disease susceptibility, guide preventive strategies, and develop clinical interventions using naturally occurring lipid products. The present invention also identifies the first non-proteinaceous hormone, C16:1n7-palmitoleate. The work presented herein harnesses high density, high resolution, quantitative lipidomics combined with functional experimentation platforms to explore systematic metabolism. The striking impact of lipid chaperones on these paradigms in vivo revealed lipid pathways that contribute to systemic metabolic homeostasis in physiologically relevant settings. In this experimental paradigm, the functional lipidomic approach was very powerful and yielded several critical and unexpected results: The impact of diet on adipose tissue lipid composition and metabolism is under strict control of adipose tissue lipid chaperones and that these molecules ensure that the dietary input is the predominant determinant of fatty acid composition in fat. In the absence of these chaperone proteins, adipose tissue is markedly refractory against the influence of diet on its lipid constituency and relies heavily on de novo lipogenesis.

Additionally, adipose tissue regulates, in a lipid chaperone-dependent manner, the metabolic activities of distant organs through its lipid output and reduces this to a specific metabolic pathway in the liver. Further, the present invention provides for a unique fatty acid, C16:1n7-palmitoleate, as a major signaling lipid that controls several metabolic activities in both liver and muscle tissues. Moreover, the present invention provides for a model of the molecular mechanisms underlying lipid chaperone biology and how these molecules regulate a lipid hormone in adipose tissue to generate remarkable effects on systemic metabolism.

Hence, an embodiment of the present invention provides for a lipid diagnostic marker, C16:1n7-palmitoleate, for monitoring metabolic homeostasis and diseases, such as diabetes and fatty liver diseases. In one embodiment, the method comprises measuring the concentration of C16:1n7-palmitoleate in the free fatty acid component of the serum of a subject, wherein C16:1n7-palmitoleate serves as an adipose-derived signaling lipid produced from the adipose tissue, and wherein a low concentration is associated with increased risk for metabolic disease. In general, a concentration of C16:1n7-palmitoleate in the free fatty acid component of the serum about two-fold below that found in normal, healthy individuals is associated with increased risk for metabolic disease. More specifically, a concentration of C16:1n7-palmitoleate in the free fatty acid component of the serum below about 12.5 µM to about 17.5 µM is a marker associated with increased risk for metabolic disease. In a related aspect, in individuals at risk for metabolic syndrome, a concentration of about 12.5 µM to about 17.5 µM in free fatty acid component of the serum indicates de novo lipogenesis and this concentration should be stimulated or provided by diet.

In another embodiment, a method for determining the status of fatty acid metabolism in a subject comprises measuring the concentration of C16:1n7-palmitoleate in the free fatty acid component of the serum of said subject, wherein said C16:1n7-palmitoleate is a biomarker for adipose-specific activation of de novo lipogenesis and suppression of liver lipid production. In a related embodiment, increased C16:1n7-palmitoleate is a biomarker of protection against metabolic syndrome or metabolic disease. For example, in individuals at risk for metabolic syndrome, a concentration of about 12.5 µM to about 17.5 µM in free fatty acid component of the serum indicates de novo lipogenesis and this concentration should be stimulated or provided by diet.

Another embodiment provides for a method for determining the status of fatty acid metabolism in a subject comprising measuring the concentration of C16:1n7-palmitoleate in the free fatty acid component of the serum of said subject as a biomarker for the activity of a nuclear receptor, such as PPAR, in the adipose tissue. In another embodiment, C16:1n7-palmitoleate is a biomarker for the activity of adipose FABP aP2, which is itself a risk factor for metabolic diseases.

Additional embodiments of the present invention provide for the uses of C16:1n7-palmitoleate: as a biomarker for adipose-specific activation of de novo lipogenesis and metabolic activity of adipose tissue; a biomarker for metabolic healthiness and robustness of adipose tissues, which can be used to determine the risk for metabolic diseases in equally obese subjects; as an insulin-sensitizing hormone that improves glycemic control/glucose metabolism; to reduce the impact of lipid-enriched diet on lipid metabolism and lipid composition; for SCD-1 suppression in liver which will provide protection from fatty infiltration of liver and insulin resistance; to stimulate/potentiate the proximal insulin-signaling pathway, including activation of insulin receptor and phosphorylation of insulin receptor substrate 1, 2 and protein kinase AKT in liver; to enhance insulin signaling in muscle tissue, regulate insulin actions in peripheral tissues, and enhance insulin sensitivity; to rescue diet-induced reduction in insulin-stimulated AKT phosphorylation, and to stimulate cellular glucose uptake; and to decrease the expression of lipogenic genes in liver, including SCD-1, fatty acid synthase (FAS), and fatty acid elongase 6 (ELOVL6), and treat fatty liver disease.

Another embodiment provides for a pharmaceutical or neutraceutical formulation comprising C16:1n7-palmitoleate. Yet another embodiment provides for a composition with therapeutic utility for treating metabolic disorders, such as diabetes and fatty liver diseases, comprising C16:1n7-palmitoleate.

DESCRIPTION OF THE DRAWINGS

FIG. 1A shows dendrograms of hierarchical clustering of subjects using significant metabolites by one-way ANOVA over all groups in each tissue. RWT: wild type mice on regular diet, HFWT: wild type mice on high fat diet, RDK: fatty acid binding protein deficient (FABP$^{-/-}$) mice on regular diet, HFDK: FABP$^{-/-}$ mice on high fat diet. FIG. 1B shows scatter plots of principal components from principal component analysis (PCA) on subjects. Only fatty acids significant (p-value<0.05) from a one-way ANOVA were included. FIG. 1C shows the strength of differences between diets in the wild type (WT) and FABP$^{-/-}$ (DK) mice over all fatty acids in all lipid classes. The line plot is the ranked p-values of the DK against those of the WT in each tissue. The bar plot conveys the percent of metabolites significantly different (p-value 0.05) between diets in the WT and DK. Color versions of figures are published in Cao et al., 134 Cell 933-44 (2008), incorporated herein by reference.

FIG. 2A shows the difference of major fatty acids in diacylglycerol, free fatty acid, phospholipid, and triglyceride fractions in adipose tissue between the means of WT and FABP$^{-/-}$ mice. FIG. 2B shows the lipid class composition analysis for free fatty acids in adipose tissue. The F-statistics from a one-way ANOVA are displayed as red diamonds over the distribution of F-statistics from permuted data. The p-values are below the heat map. The heat map displays the observed data, centered to the mean of the control group and scaled by the standard deviation of all observations, FIG. 2C shows the effect of diet on knock-out mice, reflected in the plasma free fatty acids in WT or FABP$^{-/-}$ (DK) mice. FIG. 2D presents the percentile suppression of palmitoleate by high-fat diet in adipose tissue of WT or DK mice. Error bars represent SEM.

FIG. 3A shows stearoyl CoA desaturase-1 (SCD-1) promoter-driven luciferase activities in control hepatocytes (No lipid) or hepatocytes treated with plasma lipids extracted from WT or FABP$^{-/-}$ (DK) mice.

FIG. 3B shows SCD-1 promoter-driven luciferase activities in hepatocytes treated with fatty acid mixtures resembling the ratio of plasma fatty acids from WT mice (WT Mix), DK mice (DK Mix), DK mice with the concentration of palmitoleate of WT mice (DK Mix, WT C16:1n7) or DK mice with the concentration of palmitoleate, palmitate and stearate of WT mice (DK Mix, WT C16:1n7, WT C16 C18). *: significantly different from WT mix; a and b: significantly different from DK Mix.

FIG. 3C shows insulin-stimulated AKT phosphorylation in C2C12 myotubes treated with plasma lipids extracted from WT or DK mice. Values of bar plot were determined by phospho-AKT ELISA and corresponding immunoblotting results are shown as Insets.

FIG. 3D shows monocyte chemoattractant protein-1 (MCP-1) in conditional medium of adipose explants treated with plasma lipids of WT or DK mice. FIG. 3E presents SCD-1 promoter-driven luciferase activity in hepatocytes treated with different fatty acids. All fatty acids are used at 300 µM final concentration except C16:1n7 2× is 600 µM. AA: arachidonic acid; *: significantly different from controls; a: significantly different from AA-treated cells b: significantly different from palmitate-treated cells.

FIG. 3F presents data from the immunoblotting of Flag-tagged SCD-1 in hepatocytes treated with control, palmitate and palmitoleate. Anti-tubulin blot was used as loading control.

FIG. 3G is the AKT phosphorylation in C2C12 myotubes treated with fatty acids and insulin. a: significantly different from cells treated with insulin; b: significantly different from cells treated with both insulin and palmitate. The bottom panel is the corresponding immunoblotting of total and phosphorylated AKT in cells treated with pooled lipids.

FIG. 3H is the glucose uptake in C2C12 myotubes treated with insulin or palmitoleate. Top panel is immunoblotting of C2C12 cell lysates treated with insulin or palmitoleate using anti-Glut1 or Glut4 antibodies. *: p<0.05.

FIG. 4A depicts the free fatty acid and triglyceride flux among adipose, muscle, and liver tissues. Means and SEM of palmitoleate in free fatty acids (FFA) and triglyceride (TG) in plasma and adipose, muscle, and liver tissues of WT and FABP$^{-/-}$ mice are shown. The predicted lipid flux based on the tissue lipid profile pattern is indicated by the direction of arrows. Muscle fatty acids are mainly derived from liver in the form of VLDL-associated TG and from adipose tissue in the form of FFAs. FIG. 4B shows the percentile suppression of palmitoleate by HFD in TG fraction of muscle tissue in WT or KO mice. FIG. 4C shows the total palmitoleate in liver of WT or KO mice. FIG. 4D indicates the triglycerides in liver of KO mice injected with control or SCD-1 adenoviruses. Asterisk, p<0.05. Error bars represent the SEM.

FIG. 5A shows schematics of SCD-1-1500 bp promoter. PUF: polyunsaturated fatty acid response element. FIG. 5B is the regulation of WT and mutant SCD-1 promoter activities by fatty acids. AA: arachidonic acid. FIG. 5C is the regulation of wild-type and mutant SCD-1 promoter activities by plasma lipids. Plasma lipids extracted from WT or FABP$^{-/-}$ (DK) mice were used to treat FAO cells Infected with WT or mutant SCD-1 promoter-carrying adenoviruses and luciferase assays performed as described in the Examples. FIG. 5D presents the in vivo regulation of wild-type and mutant SCD-1 promoter activities. Luciferase assays were performed on liver tissues of WT or DK mice injected with WT or mutant SCD-1 reporter carrying adenoviruses. FIG. 5E is liver gene expression in mice infused with vehicle, TG:palmitate or TG:palmitoleate. *, p<0.05.

FIG. 6A shows lipogenic gene expression in adipose tissue of WT and FABP$^{-/-}$ (DK) mice. Gene expression patterns in epididymal fat pad were determined by quantitative real-time PCR. FIG. 6B is regulation of lipogenic gene promoter activities by FABPs in differentiated adipocytes. Differentiated FABP-deficient adipocytes that expressed SCD-1 or FAS promoter were infected with GFP, aP2, or both aP2 and mal1 adenoviruses, and promoter-driven luciferase activities were determined by dual-glow luciferase system. a: significantly different from GFP-adenovirus-infected cells, b: significantly different from aP2-adenovirus-infected cells. FIG. 5C shows the regulation of lipogenic gene expression in adipose tissue of mice treated with aP2 inhibitor. Gene expressions in epididymal fat pads from mice treated with vehicle or aP2 inhibitor were determined with quantitative real-time PCR. FIG. 5D relates to the differential regulation of lipogenic gene expression in adipose and liver tissues. Levels of the mRNAs in liver and epididymal fat pad from mice fed with high-fat diet were determined with quantitative real-time PCR. ACC1, acetyl-CoA carboxylase1; FAS, fatty acid synthase; SCD-1, stearoyl-CoA desaturase; ELOVL6, fatty acid elongase 6; DGAT1, acyl-CoA:diacylglycerol acyltransferase 1. *, p<0.05.

FIG. 7A is the basal and insulin-stimulated phosphorylation of insulin receptor (IR), insulin receptor substrate-1 (IRS-1) and -2 (IRS-2) and AKT in liver of mice infused with vehicle (Veh), TG:palmitoleate (C16:1n7) or TG:palmitate (C16). Representative blots are shown and quantifications on the right are averaged results of three mice in each treatment group. FIG. 7B shows the basal and insulin-stimulated phosphorylation of insulin receptor (IR), insulin receptor substrate-1 (IRS-1), AKT and GSK in muscle tissues of mice infused with vehicle (Veh), TG:palmitoleate (C16:1n7) or TG:palmitate (C16). Representative blots are shown and quantifications on the right are averaged results of three mice in each treatment group. FIG. 7C shows basal hepatic glucose production (bHGP) of mice infused with vehicle (Veh) or palmitoleate (C16:1n7).

FIG. 7D shows the glucose infusing rate (GIR) of mice infused with vehicle (Veh) or palmitoleate (C16:1n7) during hyperinsulinemic-euglycemic clamp. FIG. 7E shows the hepatic glucose production (Clamp HGP) of mice infused with vehicle (Veh) or palmitoleate (C16:1n7) during hyperinsulinemic-euglycemic clamp. FIG. 7F shows the glucose disposal rate (RD) mice infused with vehicle (Veh) or palmitoleate (C16:1n7) during hyperinsulinemic-euglycemic clamp. FIG. 7G is the regulation of systemic metabolic responses by adipose-derived lipid hormones (Lipokines). In parallel with a variety of adipokines, specific lipids released from adipocytes in response to physiological stimuli act at remote sites including liver and muscle and regulate systemic lipid and carbohydrate metabolism. Lipid chaperones negatively regulate one of these lipokines, C16:1n7 (palmitoleate), and in the absence of these FABPs, strong flux of palmitoleate from adipose tissue to liver and muscle results in improved metabolic responses.

FIG. 11A shows cholesterol ester levels in liver and plasma of WT and FABP$^{-/-}$ mice. FIG. 11B illustrates the fatty acid composition analysis for cholesterol ester in liver. The F-statistics from a one-way ANOVA are displayed as red diamonds over the distribution of F-statistics from permuted data. The p-values are below the heat map. The heat map displays the observed data, centered to the mean of the control group and scaled by the standard deviation of all observations.

FIG. 12A shows phosphatidylcholine levels in liver and plasma of WT and FABP$^{-/-}$ mice. FIG. 12B shows the fatty acid composition analysis for phosphatidylcholine in liver. The F-statistics from a one-way ANOVA are displayed as red diamonds over the distribution of F-statistics from permuted data. The p-values are below the heat map. The heat map displays the observed data, centered to the mean of the control group and scaled by the standard deviation of all observations.

FIG. 13A shows triglyceride levels in liver and plasma WT and FABP$^{-/-}$ mice. FIG. 13B is the fatty acid composition analysis for triglyceride in plasma, liver, muscle, adipose tissue. The F-statistics from a one-way ANOVA are displayed as red diamonds over the distribution of F-statistics from permuted data. The p-values are below the heat map. The heat map displays the observed data, centered to the mean of the control group and scaled by the standard deviation of all observations.

FIG. 16A shows MCP1, TNFalpha and IL6 expression in adipose fraction. FIG. 16B shows MCP1, TNFα and IL-6 expression in stromal vascular fraction.

FIG. 22 lists the primer sequences for quantitative real-time PCR.

DETAILED DESCRIPTION

Figure 1A:
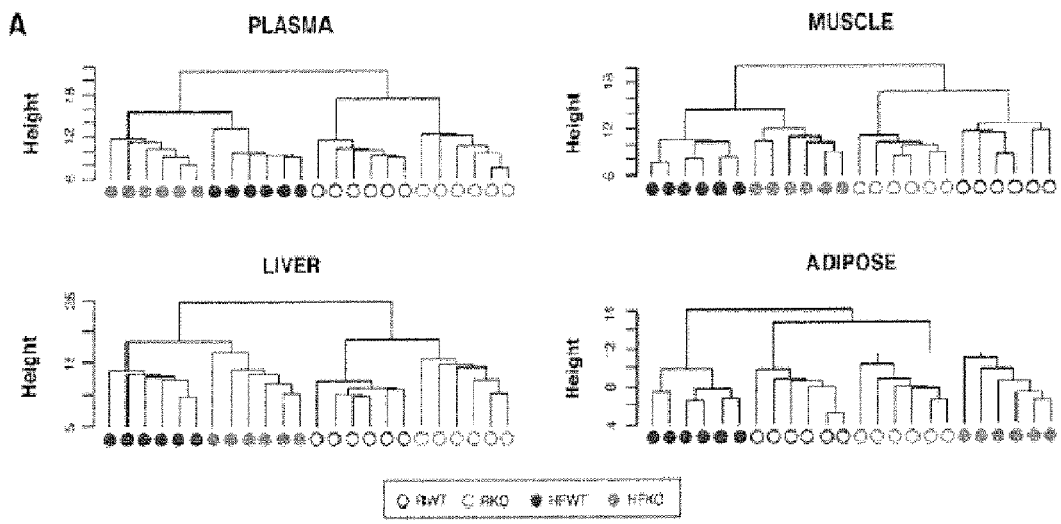
FIGS. 1A-1C relate to whole body lipid profiling.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Metabolic diseases including obesity, insulin resistance, diabetes, fatty liver disease and atherosclerosis are often related and form a disease cluster around increased adiposity, sometimes referred to as metabolic syndrome. Eckel et al., 365 Lancet 1415-28 (2005). Dysregulation of lipid metabolism has been identified as a critical contributor to the mechanistic link between these related pathologies. Ginsberg et al., 14 (S1) Obesity (Silver Spring) 41S-49S (2006). For example, increased release of free fatty acids (FFA) from adipose tissue has long been linked to muscle insulin resistance (Bergman & Ader, 11 Trends Endocrinol. Metab. 351-56 (2000), and lipogenesis and steatosis in liver. Ginsberg et al., 2006. Altered muscle lipid partitioning has also been proposed as a feature of obesity and systemic insulin resistance. Hulver et al., 2 Cell Metab. 251-61 (2005). The imbalance between liver-derived VLDL and HDL is a critical risk factor for the development of atherosclerosis and has also been linked to insulin resistance at peripheral tissues. Avramoglu et al., 368 Clin. Chim. Acta. 1-19 (2006). Epidemiological and clinical studies indicate that dietary lipids affect and sometimes even determine the course of development of metabolic syndrome. Warensjo et al., 48 Diabetologia 1999-2005 (2005).

The present invention adds an important biomarker in the characterization of fatty acid metabolism and metabolic syndrome: C16:1n6-palmitoleate. More specifically, an embodiment of the present invention comprises measuring the concentration of C16: n7-palmitoleate in the free fatty acid component of the serum of a subject, wherein C16:1n7-palmitoleate serves as an adipose-derived signaling lipid produced from the adipose tissue, and wherein a low concentration is associated with increased risk for metabolic disease. In general, a concentration of C16:1n7-palmitoleate in the free fatty acid component of the serum about two-fold below that found in normal, healthy individuals is associated with increased risk for metabolic disease. More specifically, a concentration of C16:1n7-palmitoleate in the free fatty acid component of the serum below 17.5 µM, or below about 12.5 µM is a marker associated with increased risk for metabolic disease.

Even though a growing body of evidence supports the key role of lipid metabolism in metabolic disease, the underlying mechanistic details of alterations in systemic or tissue-specific changes in lipid metabolism and how these changes are directly integrated into systemic metabolic homeostasis have not been explained fully. Many lipid species interact with fatty acid binding proteins (FABP) that act as lipid chaperones and dictate the partitioning of lipids inside cells. Several FABPs have been reported to play critical roles in systemic metabolism. Furuhashi & Hotamisligil, 7 Nat. Rev. Drug Discov. 489-503 (2008). Mice deficient in the major adipose FABP (aP2) are protected from diet-induced insulin resistance despite significant weight gain. Hotamisligil et al., 274 Sci. 1377-79 (1996). The combined deficiency of aP2 and mal1 (FABP4 and FABP5) have a profound impact on systemic metabolic regulation and render mice resistant to almost all components of metabolic syndrome including diet-induced obesity, insulin resistance, atherosclerosis and fatty infiltration of the liver. Maeda et al., 1 Cell Metab. 107-19 (2005). Liver FABP-deficient mice gain less weight under western diet and have reduced hepatic steatosis. Newberry et al., 44 Hepatology 1191-1205 (2006). Moreover, FABP expression is often changed in metabolic diseases such as atherosclerosis, type 2 diabetes, and obesity. This also applies to human disease where a genetic variation at the aP2 locus has been linked to cardiovascular disease and diabetes. Tuncman et al., 103 P.N.A.S. USA 6970-75 (2006). The critical role of FABPs in metabolic diseases was highlighted by the recent demonstration that inhibition of aP2 function through an orally active inhibitor could ameliorate metabolic syndrome in mice. Furuhashi et al., 447 Nature 959-65 (2007). Hence, uncovering the mechanisms by which FABPs regulate specific metabolic pathways and lipid mediators in the context of metabolic diseases is of critical importance.

Because most FABPs are expressed in a tissue-specific manner with highly abundant expression occurring only in a few target tissues or cells, it is generally assumed that genetic manipulation of FABP function leads to alterations in tissue lipid profiles and metabolism restricted to only those sites. Changes in lipid profiles and metabolic responses resulting from FABP-deficiency, however, especially in the case of adipose tissue FABPs, are often systemic, potentially indicating that these FABPs are part of endocrine pathway(s) that organisms have evolved to maintain overall metabolic balance most likely through their impact on lipid metabolism, trafficking, and signaling. Hence cytosolic lipid chaperones and genetic models with loss-of-function of these molecules constitute powerful experimental systems to explore unique aspects of lipid metabolism and signaling, both inside cells and between cells and organs.

An interesting example of the systemic effects of adipose tissue FABPs is the marked suppression of hepatic steaoryl-CoA desaturase-1 (SCD-1) expression observed in FABP-deficient mice. Although leptin is the most critical adipokine known to suppress hepatic SCD-1 expression (Cohen et al., 297 Science 240-43 (2002)), regulation by adipose tissue FABP-deficiency is not dependent on the action of this pathway. The same pattern of marked SCD-1 suppression in liver persists even in the ob/ob background lacking FABPs, and protects mice against liver triglyceride accumulation and insulin resistance. Cao et al., 55 Diabetes 1915-22 (2006). Furthermore, the effects of this unique regulation differ strikingly from total body SCD-1-deficiency which prevents diet-induced fatty liver disease but exacerbates diabetes in the setting of genetic obesity. Flowers et al., 56 Diabetes 1228-39 (2007).

The present approach harnessed adipose tissue lipid chaperones to explore the lipid-based pathways and signals by which local alterations in adipose tissue are connected to systemic metabolic outcomes. Utilizing high-density, quantitative lipidomic analysis of a large number of tissue and serum metabolites, as well as physiological and molecular approaches in FABP-deficient models, evidence presented herein indicates that the impact of adipose tissue on the specific composition of local and circulating FFAs is critical in determining metabolic outcomes. Additionally, the adipose tissue lipid chaperones strongly regulate lipid composition. Importantly, a specific lipid signal responsible for linking adipose tissue to systemic metabolism, palmitoleic acid C16:n17, was identified.

How metabolic syndrome interacts with de novo lipogenesis in adipose tissue has remained an unresolved issue. Schutz, 28 (S4) Int'l J. Obes. Relat. Metab. Disord. S3-S11 (2004). Evidence in recent years has suggested, however, that adipose tissue has reduced lipid synthesis capacity in obese mice and human beings. Dubois et al., 14 Obesity (Silver Spring) 1543-52 (2006); Moraes et al., 144 Endocrinol. 4773-82 (2003); Nadler et al., 97 P.N.A.S. USA 11371-76 (2000). Conversely, several genetic or pharmacological manipulations that boost de novo lipogenesis in adipose tissue are associated with improved metabolic homeostasis. Kuriyama et al., 1 Cell Metab. 41-51 (2005); Waki et al., 5 Cell Metab. 357-70 (2007).

Interestingly, even though increased de novo lipogenesis in adipose tissue leads sometimes to expansion of the fat depot, the metabolic outcomes associated with such a condition are very different from those caused by dietary obesity. Kim et al., 117 J. Clin. Invest. 2621-37 (2007); Watkins et al., 43 J. Lipid Res. 1809-17 (2002). This is also the case in FABP-deficiency, where both target tissues and the whole organism enjoy a remarkable metabolic health despite induction of dietary or genetic obesity. One explanation for this may be related to the differences in tissue and serum fatty acid profiles under the two conditions. The systemic approaches presented herein demonstrate that wild-type animals consuming a high-fat diet exhibited increased lipid content of adipose tissue, and the composition of this tissue did not differ from those of muscle or liver as the same lipids contributed to the systemic circulation. In contrast, experimentally enhanced de novo lipogenesis in adipose tissue actively alters tissue and serum fatty acids, particularly C16:1n7-palmitoleate, as is the case in the absence of adipose tissue lipid chaperones. A serum fatty acid profile with high representation of palmitoleate would contribute to improved metabolic homeostasis regardless of the total lipid mass, again a profile seen in mice lacking adipose tissue FABPs.

The results presented herein provide for C16:1n7-palmitoleate as a major signaling lipid produced from the adipose tissue. Several properties of this particular fatty acid fit well into a regulatory role as an adipose tissue-derived signal. For example, even though saturated and mono-unsaturated fatty acids of all chain lengths are produced as intermediate products of de novo lipogenesis, only C16:1n7-palmitoleate can significantly and abundantly accumulate due to enzymatic specificity of fatty acid synthase and coordinated regulation of SCD-1 and ELOVL6 enzymes. As a result, C16:1n7-palmitoleate is the only fatty acid that can substantially change serum fatty acid composition in relation to alterations in lipid metabolism in adipose tissue. Unlike its saturated counterpart palmitate, which is already highly enriched in the sn-1 position of phospholipid and triglyceride and can not be elevated further, newly synthesized palmitoleate can efficiently be incorporated into different lipid classes and dramatically alter its enrichment in a variety of compartments. The low basal levels and rapid fluctuations reflecting de novo lipogenesis again support the notion that C16:1n7-palmitoleate may serve as a regulatory signal. This characteristic also distinguishes palmitoleate also from oleate, which is very abundant in most tissues and rarely exhibits substantial concentration changes under normal physiological conditions. Hence, palmitoleate has the capacity to serve as a lipid signal that mediates communications between adipose and other tissues and, indeed, may be considered a lipokine (see FIG. 7G).

The highly coordinated regulation of lipid flux and metabolism suggests that adipose-specific activation of de novo lipogenesis might lead to a beneficial general metabolic profile through its systemic effects. If the increased products of lipogenesis in adipose tissue can efficiently suppress liver lipid production, the net outcome of adipose-specific activation of de novo lipogenesis would be anticipated to decrease body weight with improved serum lipid profile and healthier metabolic responses. This scenario is in contrast to enhanced lipogenesis in liver which often increases overall adiposity even though both conditions could have elevated serum palmitoleate. Paillard et al., 18 (6) Nutr. Metab. Cardiovasc. Dis. 436-40 (2008). This adipose-controlled lipid profile is observed in FABP-deficient mice which exhibit marked increases in the representation of C16:1n7-palmitoleate in blood and marked protection against metabolic disease, along with the benefits of SCD-1 activation in the adipose tissue to convert toxic saturated fatty acids to unsaturated ones. As similar patterns are extrapolated to humans, compositional studies support the use of this new biomarker to monitor disease susceptibility, guide preventive strategies, and lead to clinical interventions using naturally occurring lipid products. Hiraoka-Yamamoto et al., 31 (S2) Clin. Exp. Pharmacol. Physiol. S37-S38 (2004).

Additionally, the present invention demonstrates, inter alia, the impact of lipid chaperones on systemic lipid distribution and composition. The significant changes of major lipid clusters in aP2-mal1$^{-/-}$ (FABP-deficient, FABP$^{-/-}$) mice have been observed, raising the possibility that circulating lipids might regulate systemic metabolic responses in this model. Maeda et al., 2005. To explore the FABP-regulated lipid signaling networks that play a role in systemic metabolic homeostasis, high-resolution lipid analyses using lipidomics technology were performed, allowing accurate quantification of over 400 lipid species in a single sample.

Plasma and all major insulin responsive tissues were analyzed, including adipose tissue, muscle and liver from WT and FABP-deficient mice, kept on either regular or high-fat diets. To capture all FABP-deficiency or diet-driven alterations in lipid profile, unsupervised cluster analyses focusing was performed on all lipid species that exhibit statistically significant differences under any condition. Samples from tissues of individual WT or FABP$^{-/-}$ mice under the same diet segregated into tight clusters (FIG. 1A), indicating that the lipid chaperones have profound effects on systemic lipid metabolism, and that their absence in adipose tissue caused identifiable global changes in tissue lipid profiles. Moreover, the lipid profiles of plasma, liver and muscle tissues of mice on either regular or high-fat diet fell into distinctly separated clusters irrespective of genotype (FIG. 1A). This indicated that dietary lipids have greater effects than genotype on lipid composition and metabolism in these tissues. This is not an unexpected observation because dietary intake is the most critical and dominant factor that determines tissue lipid composition. Clandinin, 4 Nutrit. Res. 743-55 (1984).

Surprisingly, however, adipose tissues of FABP$^{-/-}$ mice under HFD clustered together with either genotype on regular diet (FIG. 1A), which indicates that in adipose tissue, FABP-deficiency has greater effects on lipid composition than does diet. Strikingly, mice lacking lipid chaperones on both regular and high fat diet clustered more closely compared to WT mice kept on regular diet, indicating that adipose tissue of these mice sustained a lipid profile reminiscent of lean, insulin-sensitive WT controls despite exposure to high fat diet, and dramatically differed from that of obese and insulin resistant WT animals. In other words, FABP-deficient mice were strongly resistant to the impact of diet on lipid metabolism and composition specifically in adipose tissue.

Figure 1B:
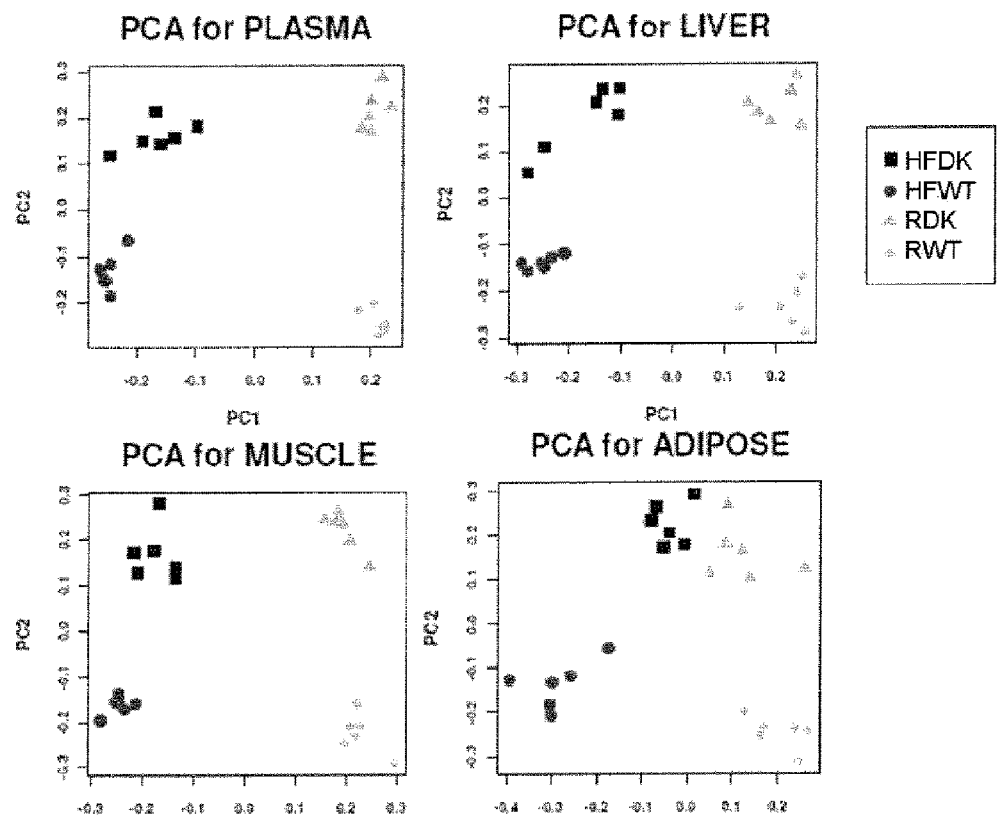

To further explore the impact of lipid chaperones on tissue responsiveness to diet, two additional approaches were used to assess dietary effects on tissue lipid composition. First, principle component analysis (PCA) was used to separate out the effects of diet (x-axis) and genotype (y-axis) on local and systemic lipid profiles (FIG. 1B). For plasma, liver, and muscle, both diet and genotype principal component effectively separated the animals into four distinct groups. For adipose tissue, however, the data points representing FABP$^{-/-}$ mice on both diets are essentially overlapping, indicating that the dietary effect on lipid composition at this site was significantly less pronounced. Even though PCA illustrated that each of the treatment groups had distinct signatures in the lipid profiles, it again supported the argument that unlike other tissues, high-fat diet failed to cause a significant change in the overall lipid profile of adipose tissue in FABP-deficient mice.

Figure 1C:
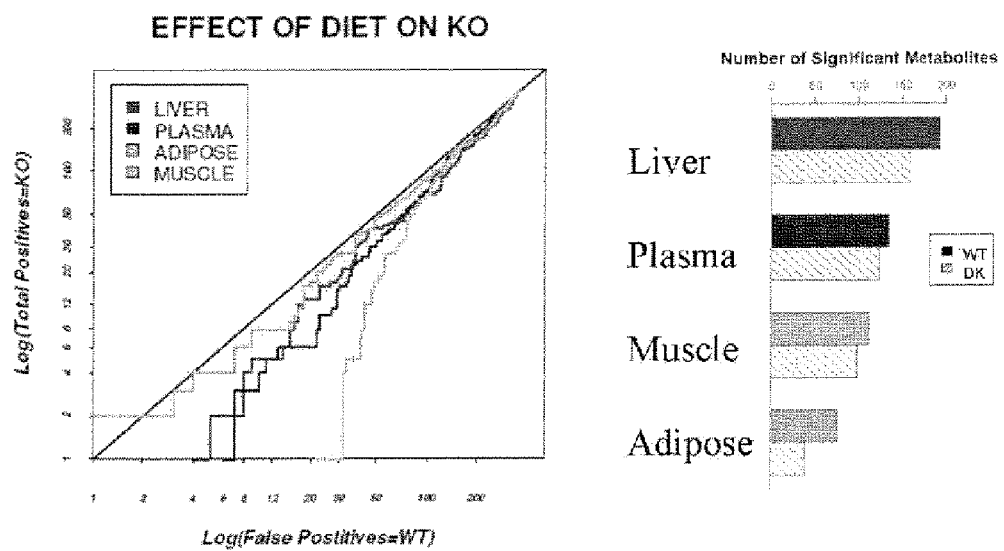
Figure 8:
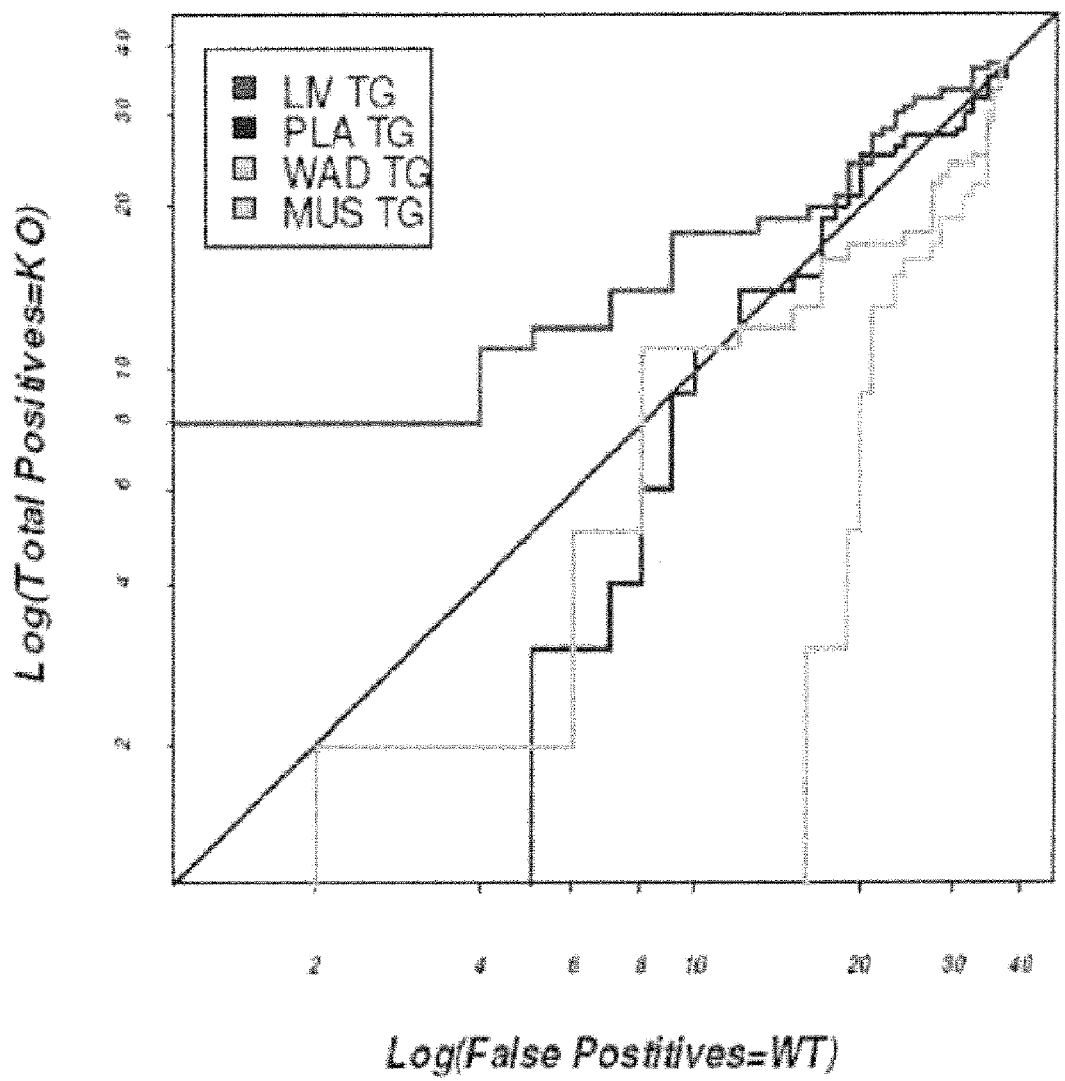
FIG. 8 shows the quantification of dietary effect on tissue triglyceride (TG) metabolism. Strength of differences between diets in the WT and FABP$^{-/-}$ (DK) mice over all fatty acids in triglycerides. The line plot is the ranked p-values of the DK against those of the WT in each tissue.

Next, the strength of the impact of diet on each genotype over all fatty acids in all lipid classes was calculated and expressed the ranked p-values against each other (FIG. 1C). This analysis did not identify differences between genotypes in the muscle tissue. In contrast, adipose tissue of FABP-deficient mice had a substantially smaller number of lipid species that are regulated by diets as compared to WT, supporting the idea that the diet had a minimal effect on adipose tissue in the absence of lipid chaperones. The number of statistically significant differences observed between diets in each genotype and in each tissue as the percent of the total number of metabolites measured was also calculated. In this analysis, adipose tissue had the largest discrepancy in the effects of diet on WT and FABP$^{-/-}$ mice (FIG. 1C). A similar property was also detected upon examination of the triglyceride (TG) component, which was dissociated from dietary intake specifically in adipose tissue of FABP$^{-/-}$ mice (FIG. 8).

These results clearly demonstrate that lipid chaperones are required intermediaries between dietary input and adipose tissue lipid metabolism because the adipose tissue of mice lacking FABPs is completely resistant to the effects of high-fat diet induced lipid compositional changes. This is an unprecedented and remarkable result because even loss-of-function in genes that are directly involved in lipid metabolism can rarely render tissue lipids resistant to dietary effects.

Figure 2A:
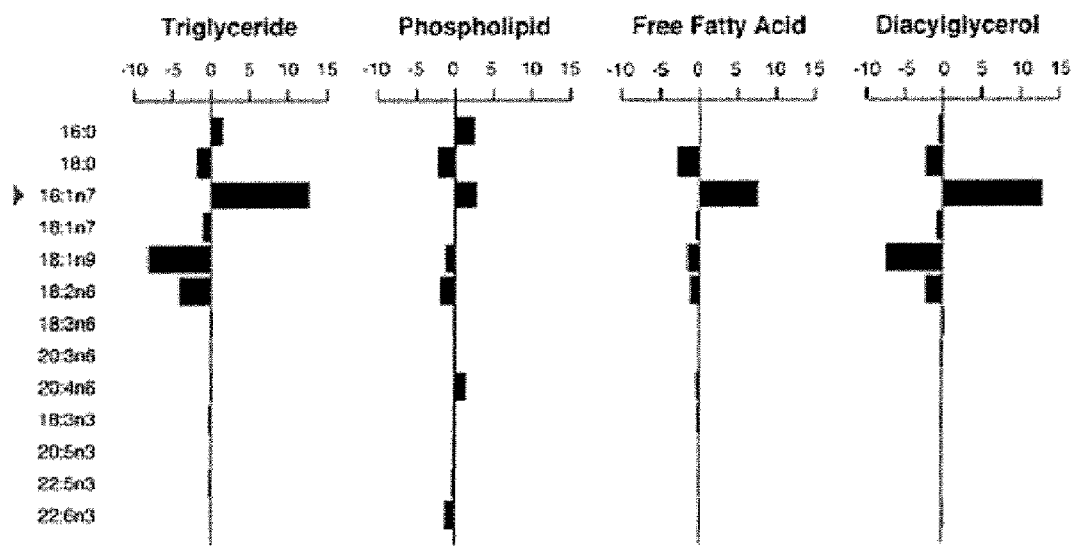
FIGS. 2A-2D present data of adipose de novo lipogenesis and plasma palmitoleate.
Figure 2B:
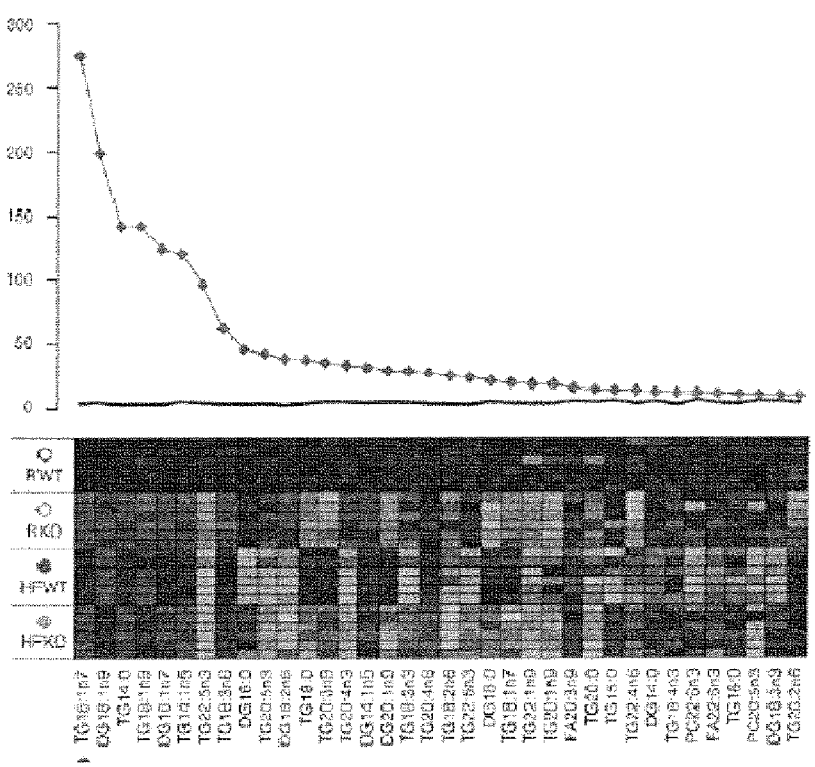

Enhanced de novo lipogenesis in adipose tissue leads to dramatically increased plasma C16:1n7-palmitoleate. Because adipose tissue of FABP-deficient mice is also resistant to diet-induced insulin resistance, the unique lipid profile observed in these mice suggested a direct link between lipid metabolism and lipid composition and the improved metabolic responses in these animals. Therefore, the lipid profile of this tissue was examined in detail. These experiments, revealed a striking enrichment of one particular fatty acid, C16:1n7-palmitoleate (FIG. 2A), in all four major lipid classes analyzed in adipose tissues of FABP$^{-/-}$ mice including free fatty acid, diacylglycerol, triglyceride, and phospholipid fractions. In fact, C16:1n7-palmitoleate was by far the most significantly regulated lipid species of all lipid groups in adipose tissue (FIG. 2B). This observation is interesting because C16:1n7-palmitoleate is a very unique fatty acid that serves as a marker of de novo lipogenesis, a process that converts glucose to fatty acids in contrast to assembling fatty acids into triglyceride. The levels of C16:1n7-palmitoleate in the diet are low and consequently its concentration in animal tissues are minimal, although concentrations can quickly and substantially increase upon activation of de novo lipogenesis. This pattern suggests a potential metabolic regulatory role for palmitoleate, and warrants further harnessing of its mechanism of action and effects on biological outcomes.

Figure 2C:
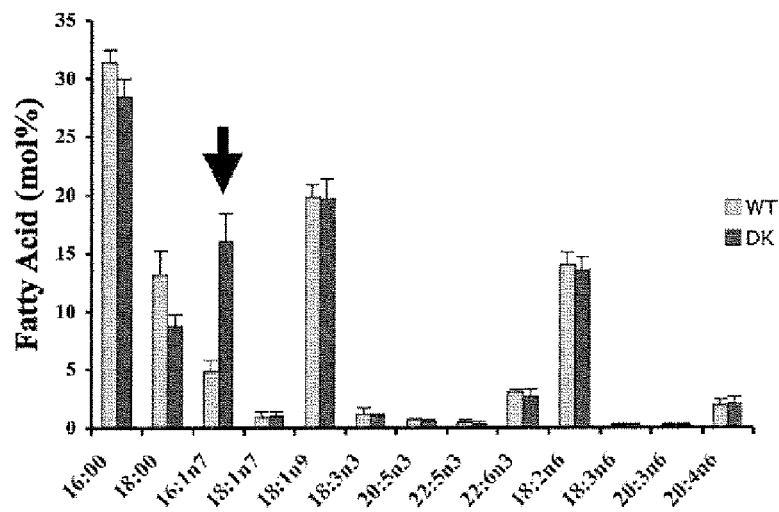
Figure 9:
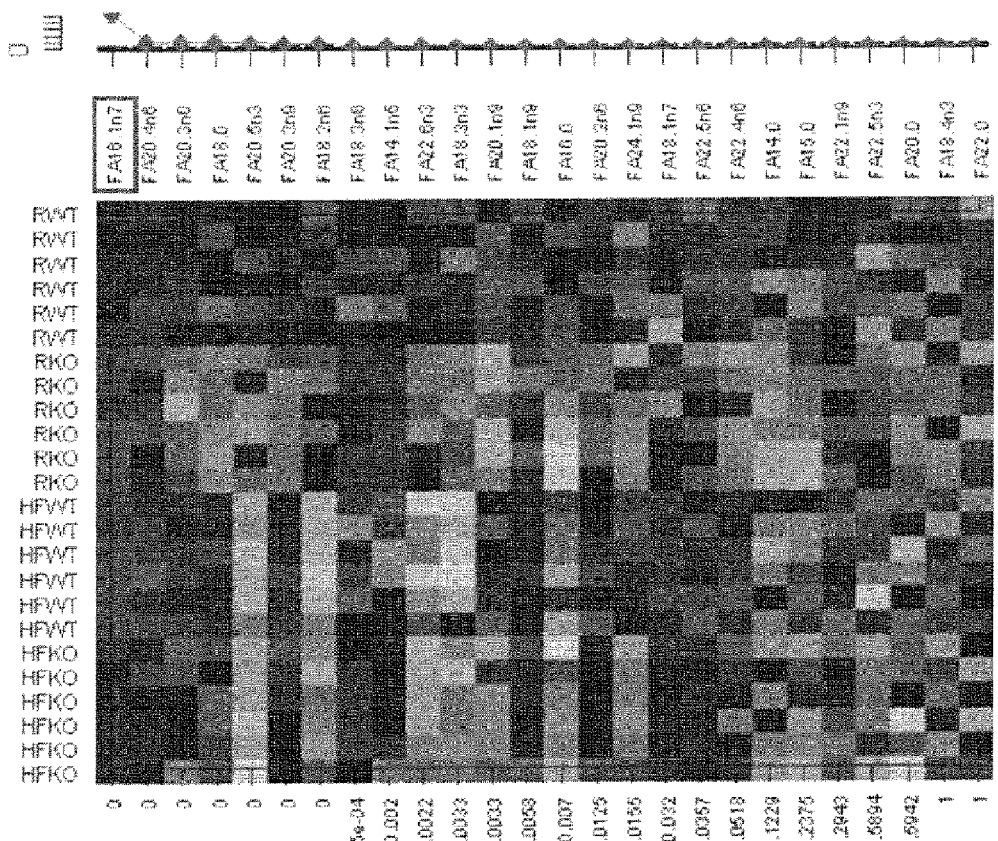
FIG. 9 is the lipid class composition analysis of plasma free fatty acids of WT or FABP$^{-/-}$ mice. The F-statistics from a one-way ANOVA are displayed as red diamonds over the distribution of F-statistics from permuted data. The p-values are below the heat map. The heat map displays the observed data, centered to the mean of the control group and scaled by the standard deviation of all observations.
Figure 10:
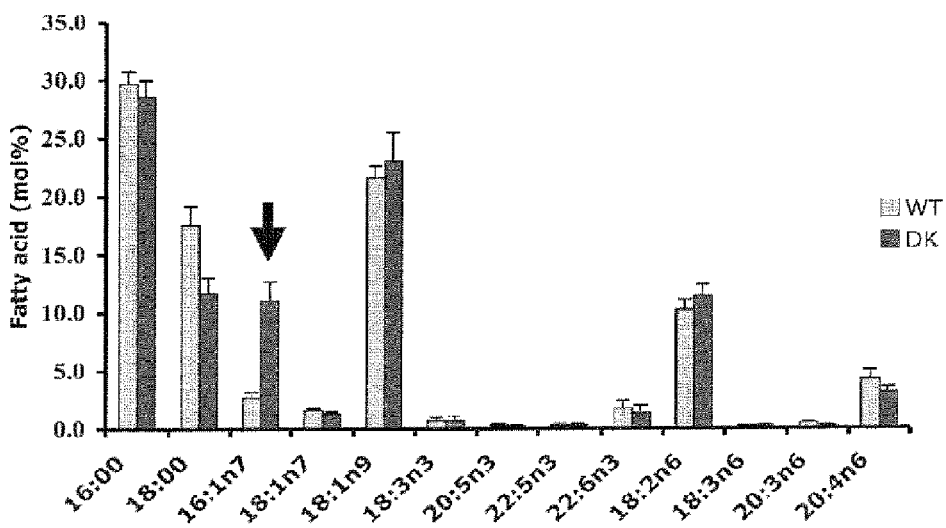
FIG. 10 illustrates plasma fatty acid profiles of WT and FABP$^{-/-}$ mice on high-fat diet. Plasma free fatty acids of WT and FABP$^{-/-}$ mice on high-fat diet were determined as described in the Examples and expressed as in FIG. 2C.

Adipose tissue is the major source of circulating free fatty acids (FFAs), and alterations in adipose lipid metabolism are often reflected in plasma FFAs. To probe the impact of adipose tissue FABPs on plasma lipids, systematic comparisons of all plasma FAAs in FABP$^{-/-}$ versus WT mice were ranked based on the statistical significance of their differences. Interestingly, palmitoleate ranked at the top among all regulated lipids (FIG. 9). Plasma palmitoleate concentration was increased in FABP$^{-/-}$ mice under both regular and high-fat diets and the magnitude of the absolute quantitative increase is very substantial, rendering palmitoleate as the third most abundant FFA in the plasma of FABP-deficient animals (FIGS. 2C and 10).

Figure 2D:
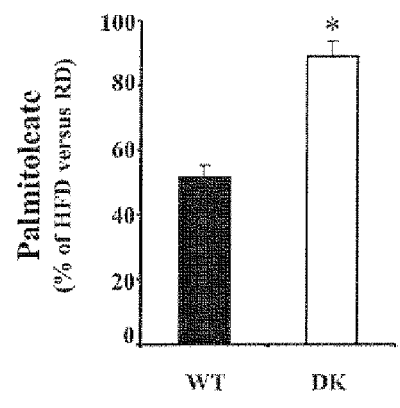
Figure 11A:
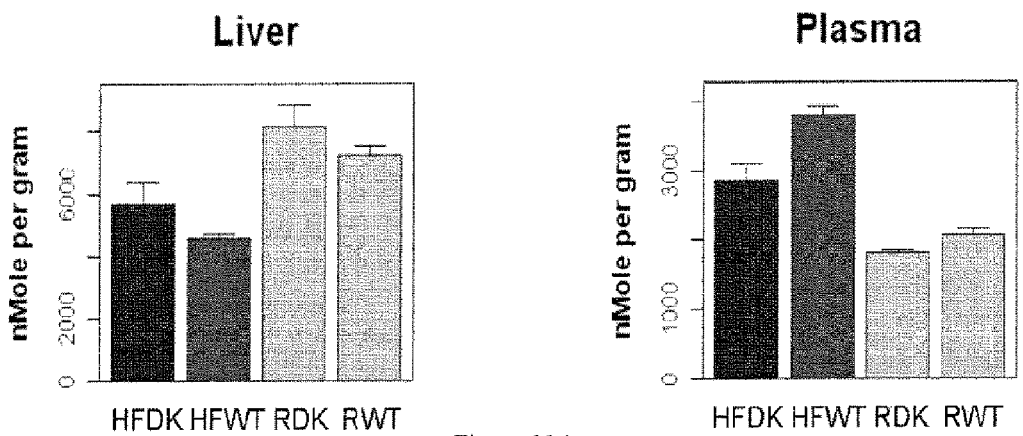
FIGS. 11A and 11B present data on cholesterol ester metabolism in WT and FABP$^{-/-}$ mice.
Figure 11B:
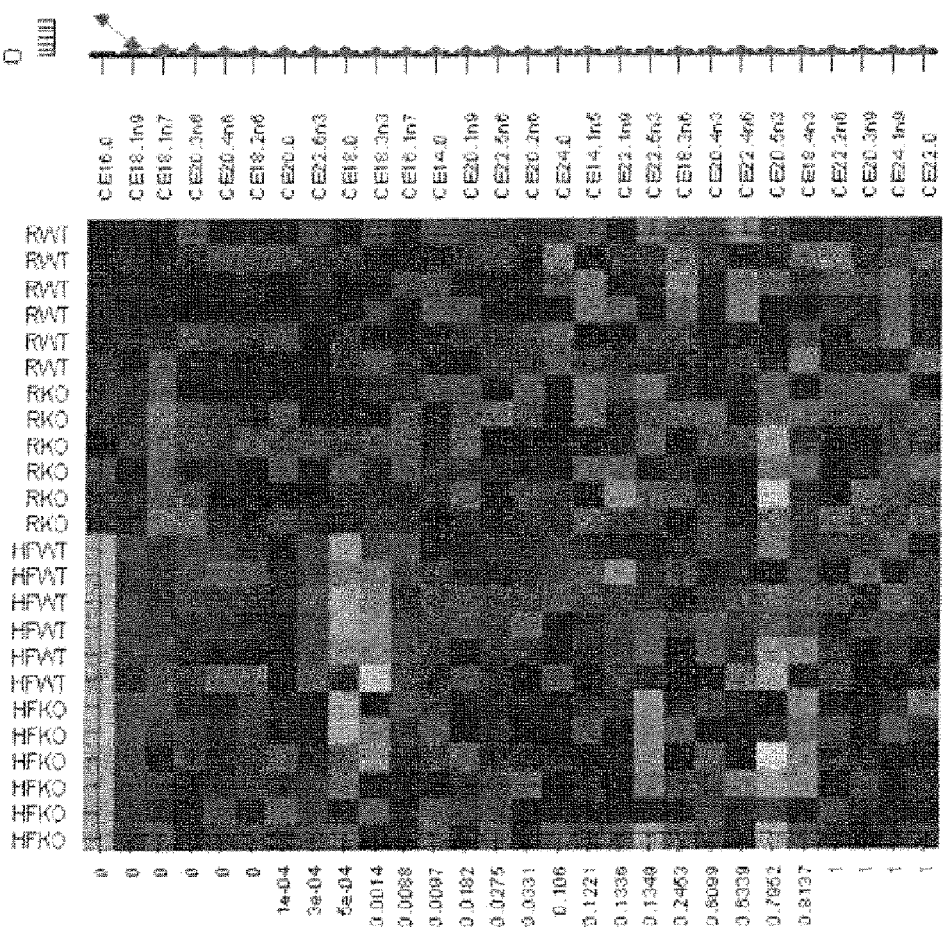
Figure 12A:
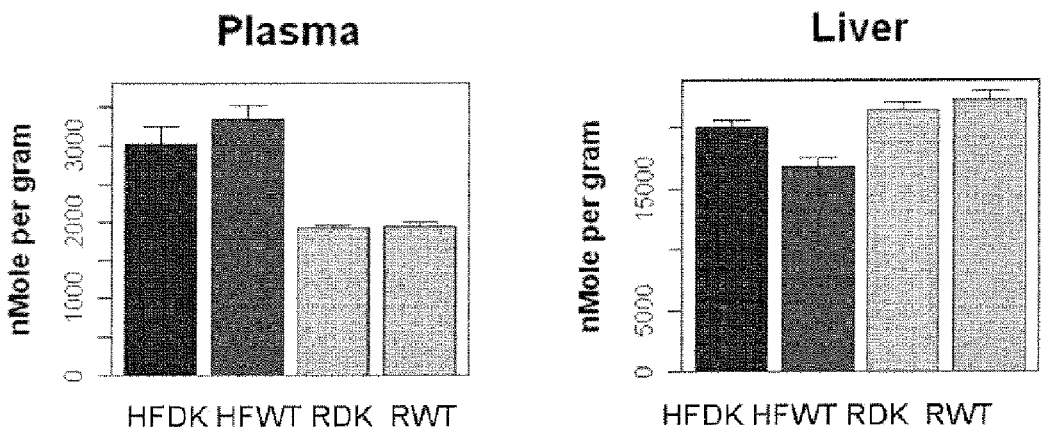
FIGS. 12A and 12B present data on phosphatidylcholine metabolism in WT and FABP$^{-/-}$ mice.
Figure 12B:
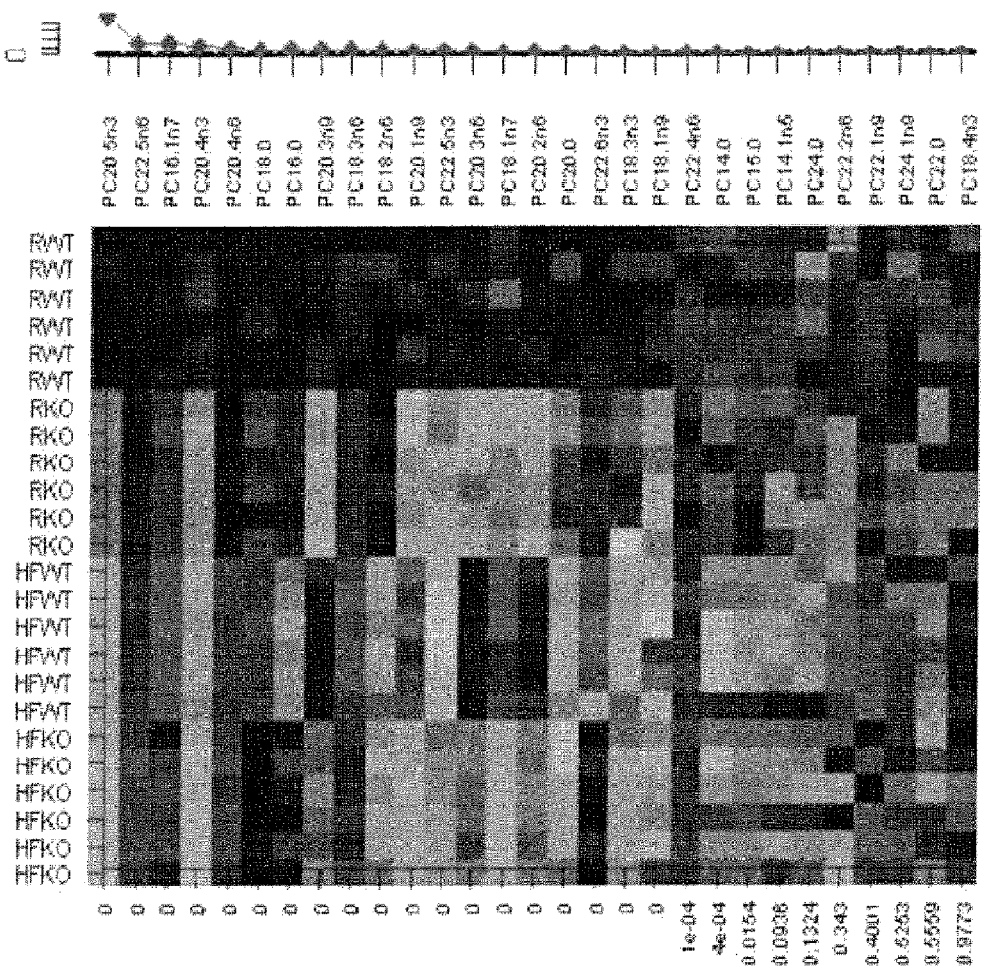
Figure 13A:
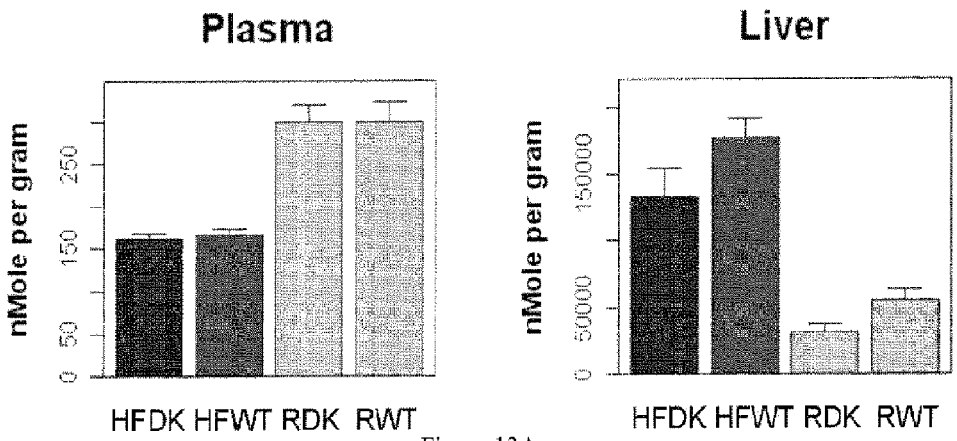
FIGS. 13A and 13B illustrate the triglyceride metabolism in WT and FABP$^{-/-}$ mice.
Figure 13B:
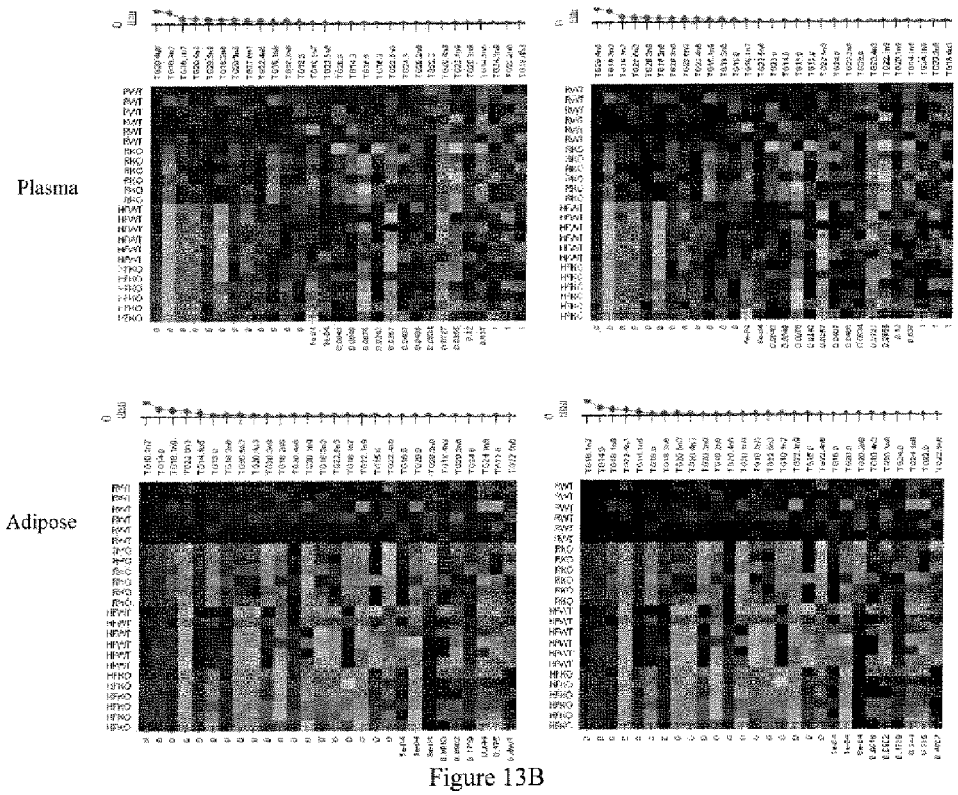
Figures 14, 15:
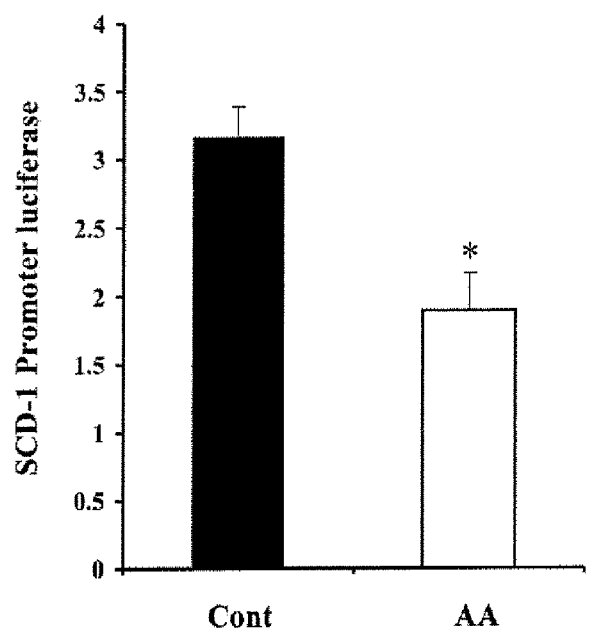
FIG. 14 shows palmitoleate in adipose tissue of WT or FABP$^{-/-}$ mice under either regular or high-fat diets. The differences among groups were calculated using Post-hoc comparisons to specifically capture the pair-wise effects of high-fat diet on WT or FABP$^{-/-}$ mice.
FIG. 15 illustrates the regulation of SCD-1 promoter activity by polyunsaturated fatty acids (PUFA) in hepatocytes. FAO hepatocytes were infected with SCD-1 promoter reporter-carrying adenoviruses and treated with arachidonic acid (AA) at 300 µM overnight. Promoter activity was determined by measuring luciferase activity.

This observation led to the investigation of the possibility that increased adipose and serum palmitoleate is both a critically important and a functionally significant change in lipid metabolism in FABP-deficient mice, possibly supporting their improved systemic energy homeostasis. Additionally, all essential lipid species including triglycerides, phospholipids, and cholesterol esters in individual tissues as well as their systemic regulatory patterns were analyzed (FIGS. 11, 12 and 13), and did not reveal any major change in these metabolic pathways. Furthermore, total palmitoleate in adipose tissue of WT mice was reduced by nearly 50% upon exposure high fat diet but this reduction was only 10% in FABP-deficient animals, demonstrating that FABP-deficiency produces marked resistance to dietary regulation of palmitoleate adipose tissue (FIG. 2D). Post-hoc comparisons in the lipidomic analysis, showed a statistically significant and dramatic decrease of palmitoleate triglyceride compartment of adipose tissue in WT mice on high fat diet compared controls on regular diet (FIG. 14). In contrast, there was no difference in palmitoleate between FABP$^{-/-}$ mice on either diet. Examination of plasma lipid profiles indicated that the resistance to dietary suppression of palmitoleate production in FABP$^{-/-}$ mice was also reflected in plasma (FIG. 10). In short, increased palmitoleate in adipose tissue and plasma is the most significant change in overall lipid metabolism in FABP$^{-/-}$ mice.

The present invention provides for an increase in C16:1n7-palmitoleate in plasma lipids, which contributes to metabolic regulation. Obesity-induced increases in circulating FFAs have been linked to peripheral insulin resistance and enhanced triglyceride synthesis and lipid accumulation in liver. Paradoxically, FABP$^{-/-}$ mice have significantly higher total plasma FFAs compared to WT controls, and yet they maintained superior insulin sensitivity under both regular and high-fat diets and were completely protected against fatty liver disease. Maeda et al., 2005. Neither adiponectin nor leptin plays a significant role in this metabolic profile and the improved whole-body metabolism observed in FABP$^{-/-}$ mice (Cao et al., 2006), raising the possibility that C16:1n7-palmitoleate might be the signal emerging from adipose tissue to improve systemic metabolic outcomes in FABP-deficiency.

This possibility was tested using several highly sensitive assays to probe the functional profile and activities of plasma lipids. SCD-1 was chosen as a target because it was determined previously that the suppression of hepatic SCD-1 activity is a major alteration in FABP-deficient mice under diet-induced or genetic obesity. Cao et al., 2006; Maeda et al., 2005. Hepatic SCD-1 expression is regulated by a variety of hormones and nutritional factors such as insulin, glucose, and polyunsaturated fatty acids (PUFAs). Ntambi & Miyazaki, 43 Prog. Lipid Res. 91-104 (2004). Examination of DNA sequences 1.5 kb upstream of the SCD-1 transcription initiation site has revealed transcription factor binding elements that are sufficient for insulin and polyunsaturated fatty acids (PUFA) regulation of this promoter. Chu et al., 26 Mol. Cell Biol. 6786-98 (2006); Ntambi, 40 J. Lipid Res. 1549-58 (1999). The 1.5 kb murine SCD-1 promoter was placed in front of a luciferase reporter and inserted into an adenovirus construct. FAO rat hepatoma cells infected with this adenovirus verified the responsiveness of this reporter to PUFA, consistent with previous observations (FIG. 15). Because this assay system was adapted to a microplate format, very small amounts of lipids were required for experimentation. This system allowed direct testing for the effects of lipids extracted from plasma of WT and FABP-deficient animals.

Figure 3A:
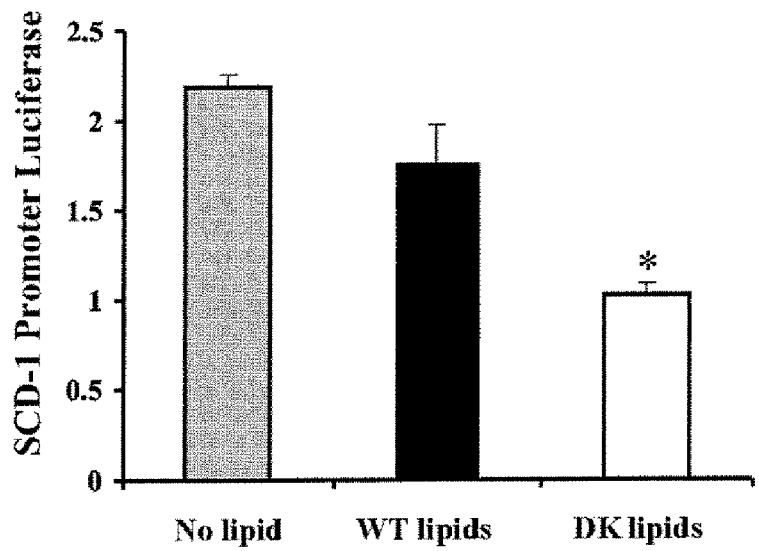
FIGS. 3A-3H present data related to the metabolic regulation by plasma lipids.

Lipids were extracted from whole plasma and applied to liver cells expressing the SCD-1 promoter reporter gene. Although SCD-1 promoter activity in liver cells treated with lipids from WT plasma showed little difference from non-treated cells, the activity of cells treated with lipids extracted from FABP-deficient plasma was reduced by 40% (FIG. 3A). These results indicate that plasma lipids from FABP-deficient mice carry an activity that suppresses SCD-1 expression in liver cells. To control for any difference in the amount of lipids extracted from plasma and to mimic the in vivo regulation of SCD-1 expression, mixtures of FFAs were generated with the same molar ratio detected in WT or FABP-deficient plasma lipids using the major fatty acids listed in FIG. 2C.

Figure 3B:
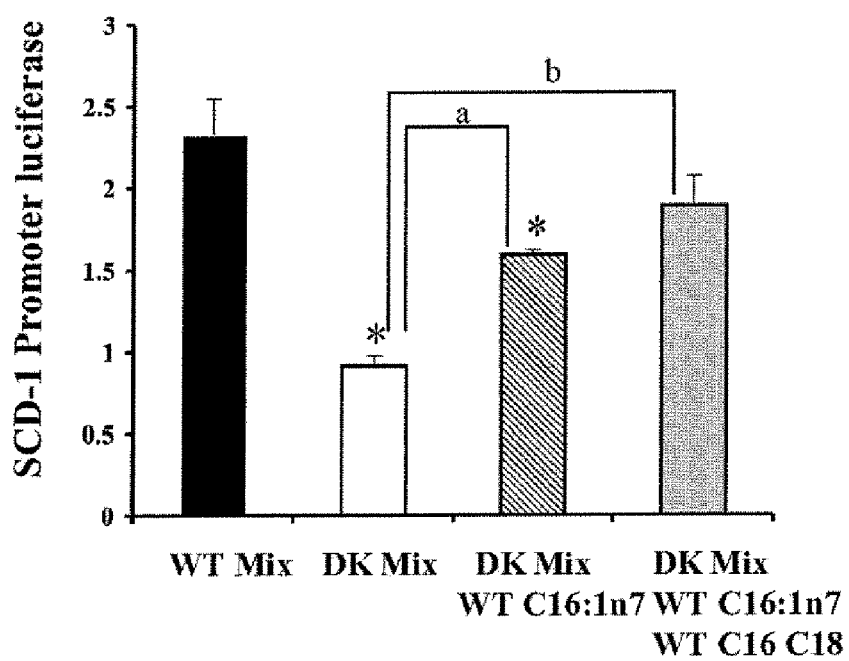

Interestingly, these lipid mixtures exerted the same pattern of activity as their corresponding plasma composition: a lipid mixture mimicking FABP-deficient plasma composition suppressed the SCD-1 promoter whereas the mixture representing WT lipids lacked suppression activity (FIG. 3B). When the high concentration of palmitoleate in the lipid mixture mimicking the plasma of FABP$^{-/-}$ mice was reduced to the level seen in WT controls without changing other lipid components or total content, the SCD-1-suppressing activity was also significantly diminished (FIG. 3B). FABP-deficient mouse plasma fatty acids also exhibit slight reductions in palmitate and stearate (FIG. 2C), perhaps explaining the residual activity retained in DK-mimicking lipid mixture to suppress SCD-1 promoter after the reduction of palmitoleate. Indeed, after adjustment of these two lipid quantities in DK lipid mixture to WT levels, the SCD-1-suppressing activity was lost completely (FIG. 3B). These results demonstrate that C16:1n7-palmitoleate is the main lipid component contributing very significantly to the regulation of SCD-1 expression.

Figure 3C:
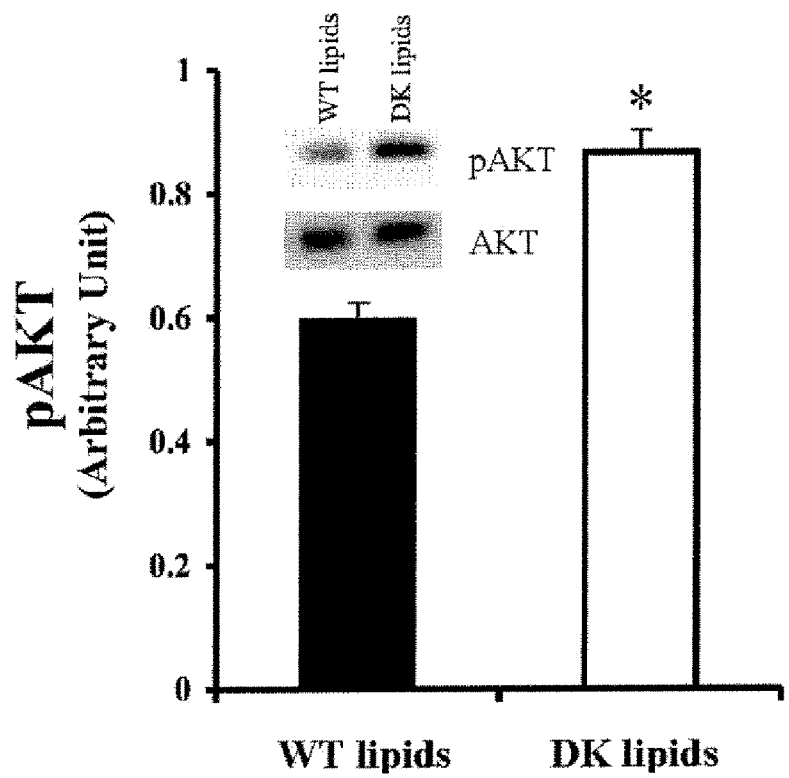

In addition to the liver phenotypes described above, significantly improved whole body glucose disposal with increased muscle glucose uptake was observed in the FABP$^{-/-}$ mice. To investigate whether plasma lipids also played a role in regulating muscle insulin action, differentiated C2C12 myotubes were treated with lipid extracts from each genotype and the insulin-stimulated AKT phosphorylation determined using an ELISA system. Myotubes pretreated with plasma lipids extracted from FABP-deficient mice had significantly enhanced AKT phosphorylation upon insulin treatment compared to those exposed to WT lipids (FIG. 3C). This result indicated that the unique plasma lipid profile of FABP$^{-/-}$ mice might also play a role in the insulin sensitizing effect of FABP-deficiency on muscle tissue. ELISA results were confirmed by western blots using lipids pooled from multiple mice that showed similar effects of DK-derived plasma lipids on AKT phosphorylation (FIG. 3C Inset).

Figure 3D:
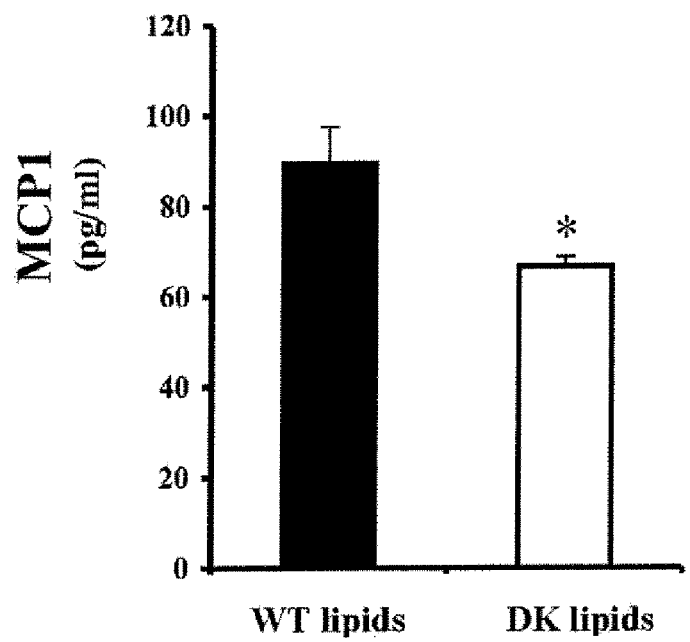
Figure 16A:
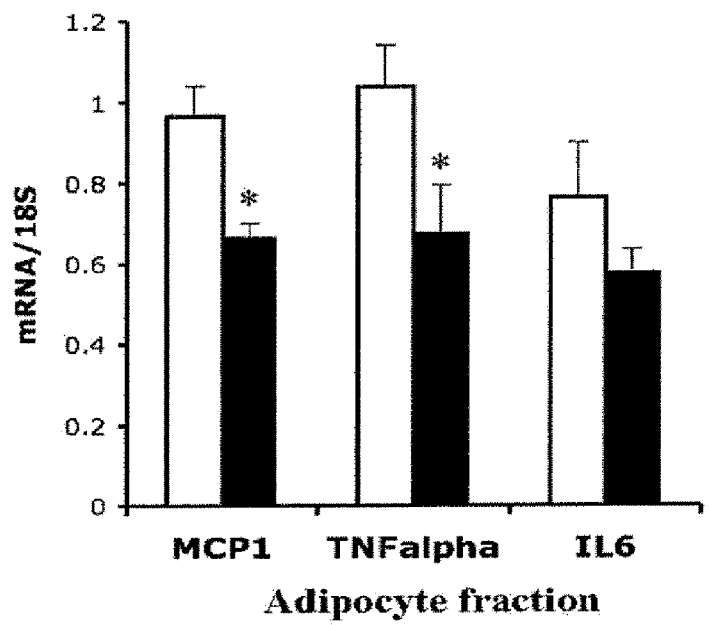
FIGS. 16A and 16B present cytokine expression in adipocyte and stromal vascular fractions treated with fatty acids. Epidydamal fat pads were dissected from WT mice and separated into adioycte and stromal vascular fractions as described in Experimental Procedures. Each fraction was treated with palmitate or palmitoleate at 500 µM for 2 hrs. Gene expression was determined with quantitative real-time PCR.
Figure 16B:
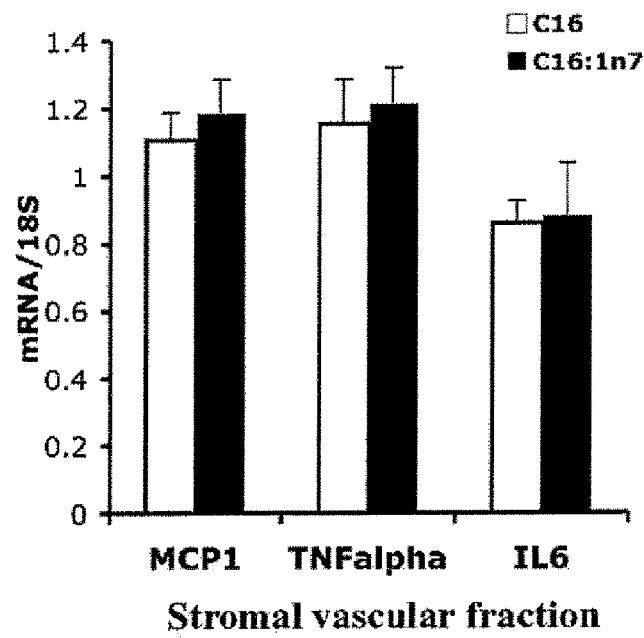

Obesity is associated with low-grade inflammation and increased inflammatory activities in liver and adipose tissues contribute to the development of systemic insulin resistance. Hotamisligil, 444 Nature 860-67 (2006). The effect of plasma lipids on adipose tissue inflammatory responses was explored using explants of adipose tissue treated with lipids from WT or FABP$^{-/-}$ mice. MCP-1 secretion from adipose explants treated with WT lipids was significantly higher than those treated with lipids from FABP$^{-/-}$ animals (FIG. 3D), indicating that these lipids also have the ability to regulate adipose tissue inflammatory output as indicated by MCP-1 production. Because adipose tissue contains multiple cell populations in addition to fat cells, adipose tissue was separated into adipocytes and stromal vascular fractions, and each fraction treated with either palmitate or palmitoleate. Interestingly, palmitoleate suppressed cytokine expression in adipocyte fractions as compared to palmitate, but the two lipids have similar effects on stromal vascular cells (FIG. 16). Collectively, these experiments demonstrated that lipid components of plasma carry multiple metabolic activities which are significantly modulated by adipose tissue lipid chaperones as a result of alterations in lipid metabolism and action.

Figure 3E:
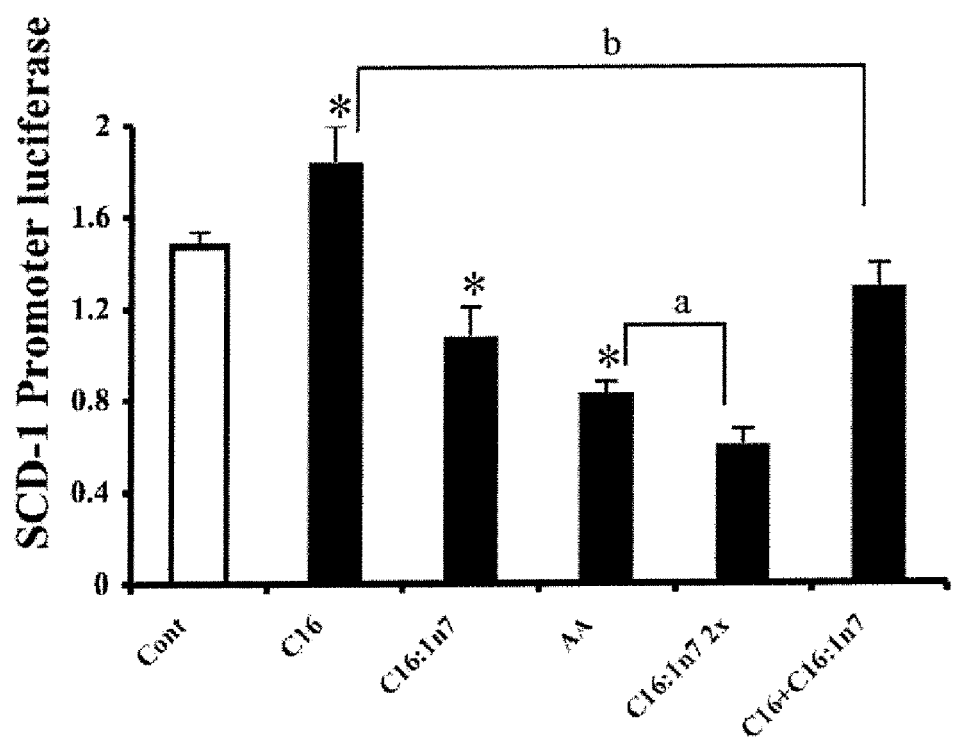
Figure 3F:
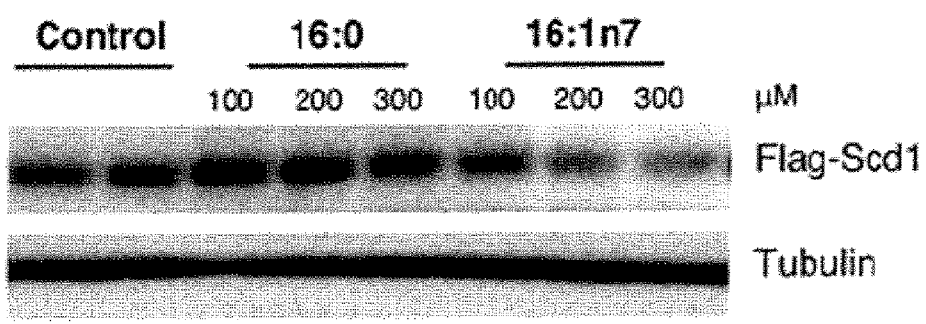

The observations reported herein also raised the possibility that C16:1n7-palmitoleate might be the lipid species responsible, at least in part, for the metabolic activities linked to adipose tissue FABPs. Hence, C16:1n7-palmitoleate, along with several lipids to serve as controls, was used to treat liver cells expressing the SCD-1 promoter reporter. In this setting, palmitate increased SCD-1 promoter-driven reporter activity, and palmitoleate negatively regulated this promoter (FIG. 3E). Interestingly, palmitoleate also antagonized the effect of palmitate on SCD-1 promoter in cells treated with a mixture of the two lipids. The suppressive impact of palmitoleate on SCD-1 promoter activity was comparable to arachidonic acid (AA), the well-established lipid mediator known to suppress SCD-1 expression. Because palmitoleate is nearly ten-times more abundant in the plasma of FABP$^{-/-}$ mice than is AA (FIG. 2C), it is most likely accounts for the suppression of SCD-1 under physiologically relevant conditions. The effects of palmitoleate on the levels of SCD-1 protein, which is known to have a very short half-life (Heinemann & Ozols, 68 Prostaglandins Leukot. Essent. Fatty Acids 123-33 (2003)), were also examined. To do this, a Flag-tagged SCD-1 from the CMV promoter was constructed that is not significantly regulated by lipids. Palmitate stabilized SCD-1, but palmitoleate significantly increased SCD-1 protein degradation (FIG. 3F). This observation suggested that palmitoleate regulates SCD-1 abundance via several parallel mechanisms, which may collectively cause the dramatic suppression of liver SCD-1 activity in FABP-deficient mice. Maeda et al., 2005.

Figure 3G:
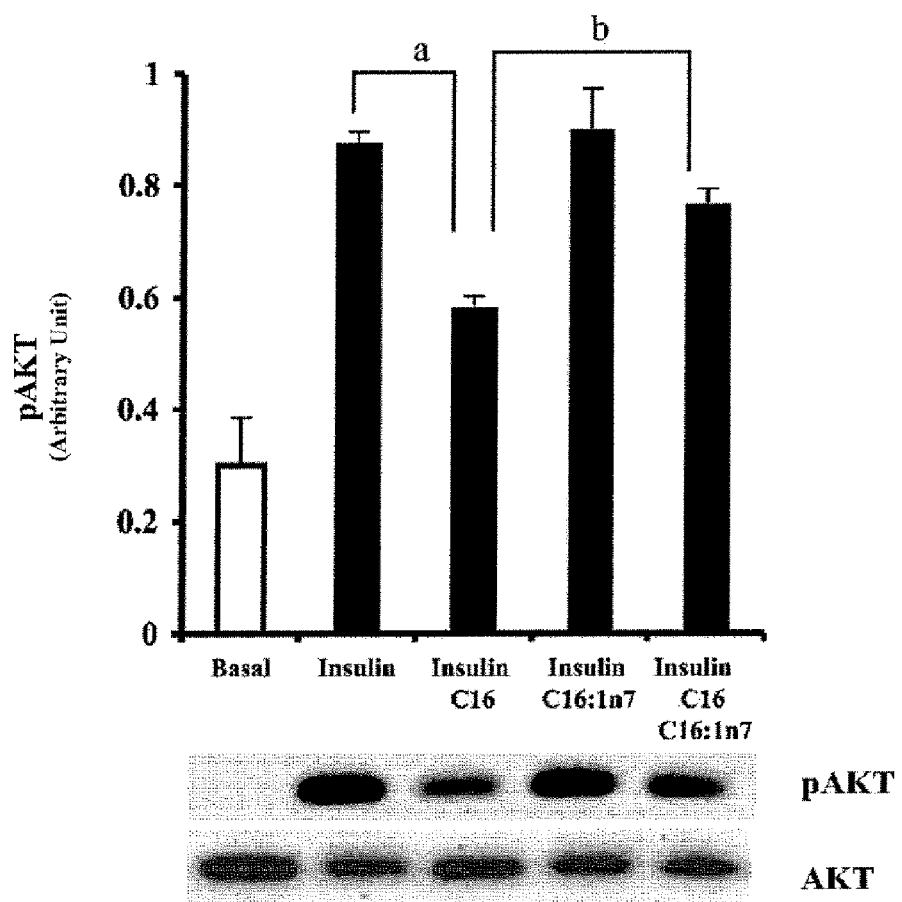
Figure 3H:
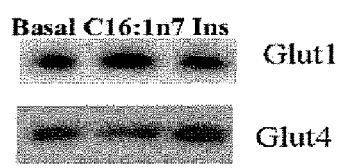
Figure 3H:
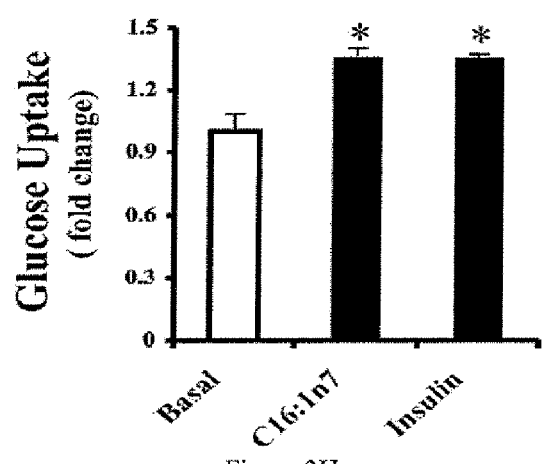

The effect of C16:1n7-palmitoleate on muscle insulin signaling was explored by pre-treating C2C12 myotubes with either palmitate or palmitoleate overnight and then stimulating the cells with insulin. Palmitate significantly reduced insulin-stimulated AKT phosphorylation. Conversely, C16:1n7-palmitoleate had little effect on its own in this in vitro setting (FIG. 3G). When cells were co-treated with both palmitate and palmitoleate, however, palmitoleate rescued the palmitate-induced reduction in insulin-stimulated AKT phosphorylation. Moreover, C16:1n7-palmitoleate itself stimulated glucose uptake into C2C12 cells to a level similar to insulin (FIG. 3H). The mechanism of this increase is not, apparently, associated with alterations in the absolute levels of Glut1 and Glut4 proteins (FIG. 3H).

Figure 4A:
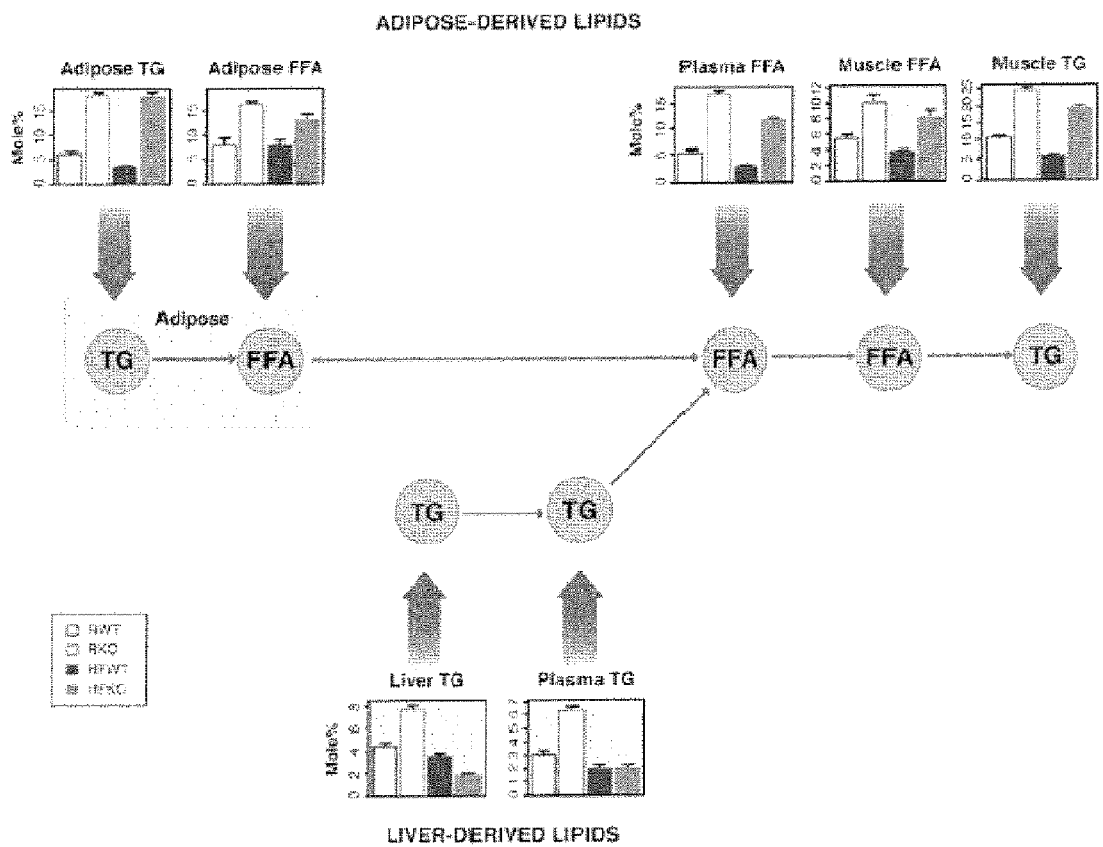
FIGS. 4A-4D present information related to the systemic palmitoleate metabolism.

Whole body metabolism of palmitoleate supports its role in systemic metabolic regulation. The potential effects of palmitoleate in metabolic homeostasis were studied by examining the metabolism of palmitoleate in muscle and liver in relation to those derived from adipose tissue by utilizing lipidomic and informatic tools. Muscle lipids are mainly derived from adipose tissue in the form of FFAs, and liver in the form of VLDL-associated triglyceride (FIG. 4C). Even though muscle lipid accumulation and metabolism are highly related to insulin resistance at this site, current technology is still unable to trace lipid fluxes under normal physiological conditions. The unique lipid paradigm revealed by the systemic lipid profiling in this study, however, allowed the modeling and examination of lipid fluxes among key tissues engaged in lipid and glucose metabolism. Levels of C16:1n7-palmitoleate in FFA fractions were compared, revealing that the level of muscle palmitoleate was intimately associated with that of plasma, which was itself a direct reflection of adipose FFAs (FIG. 4A).

Figure 4B:
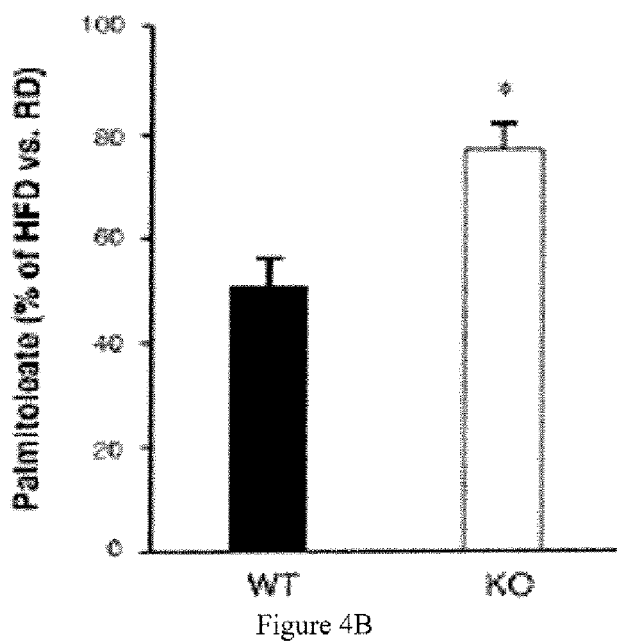
Figure 4C:
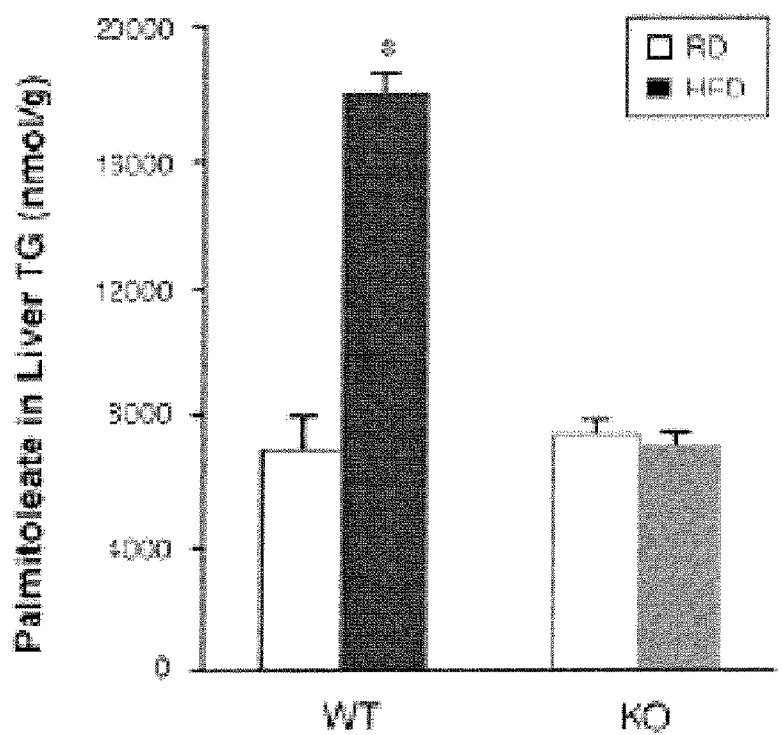
Figure 4D:
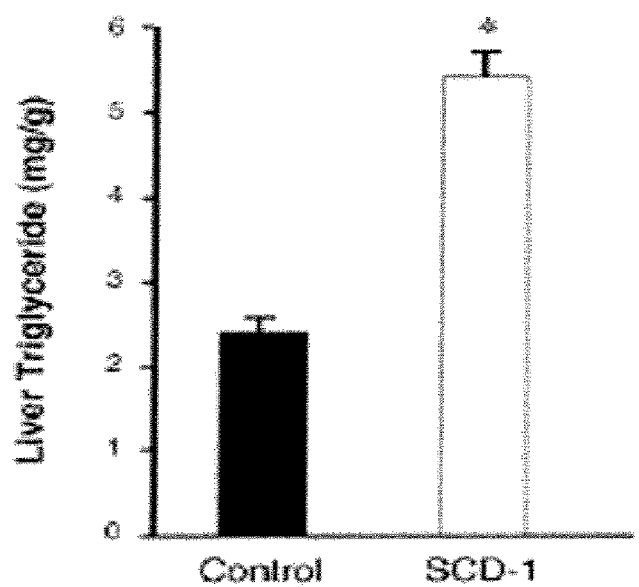
Figure 17:
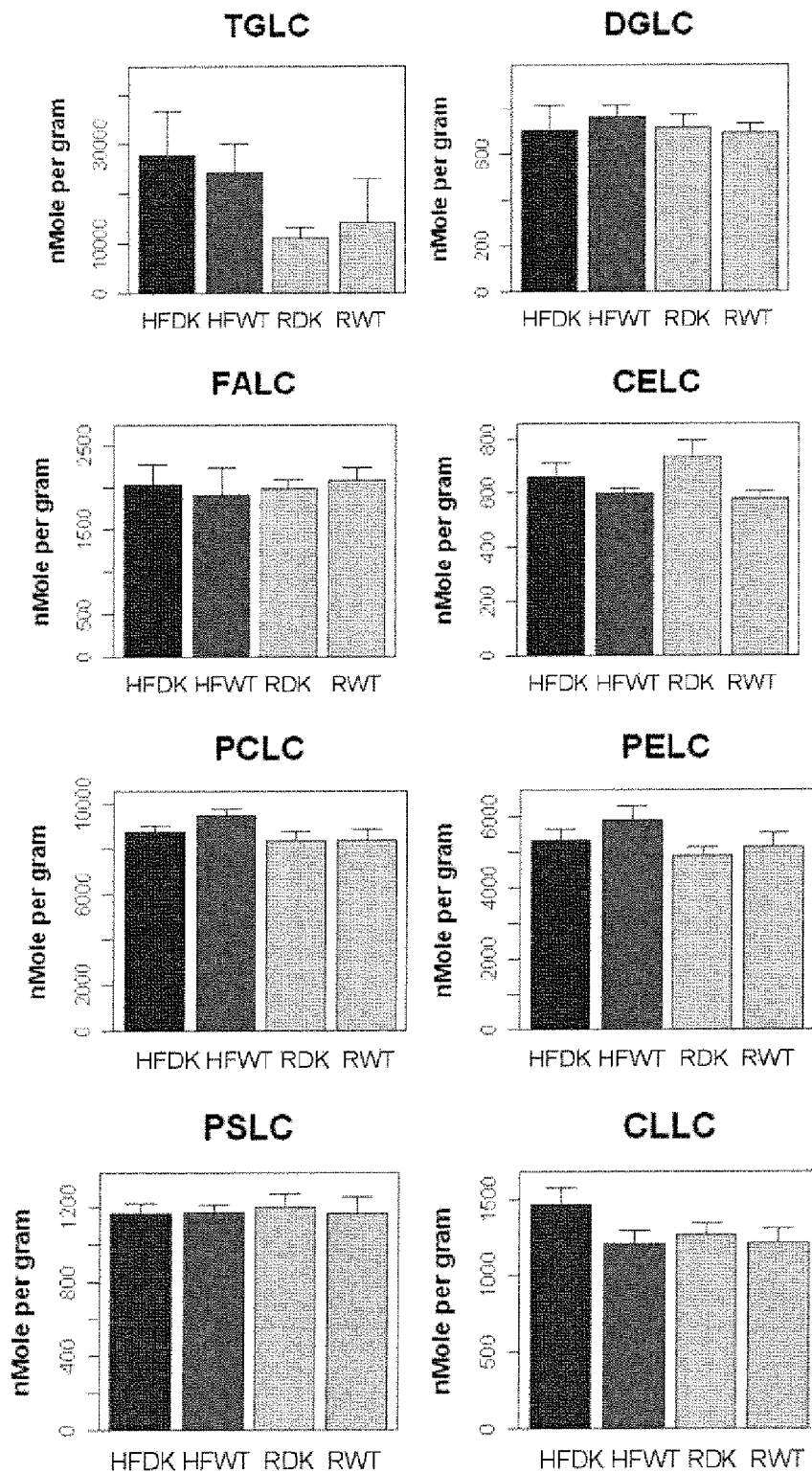
FIG. 17 shows the lipid metabolism in muscle tissue of WT or FABP$^{-/-}$ mice. Lipids from muscle of WT or FABP$^{-/-}$ mice were quantified as described in Examples and expressed as nmol per gram. LC: long chain fatty acid, TG: triglyceride, DG, diacylglycerol, FA, fatty acid, CE, cholesterol ester, PE: phosphatidylethanolamine, PS: phosphatidylserine, PC: phosphatidylcholine, CL: cardiolipin.

In contrast, C16:1n7-palmitoleate in the muscle triglyceride (TG) fraction showed a clear difference from the pattern of plasma TG palmitoleate that was derived from liver (FIG. 4B). These results suggest that the strong flux of palmitoleate from adipose tissue to muscle is the underlying mechanism for palmitoleate enrichment of this site in FABP$^{-/-}$ mice. Consequently, palmitoleate levels were reduced in WT muscle by high-fat diet; this reduction also occurred in FABP$^{-/-}$ mice but to a significantly less extent (FIG. 4D), a pattern that matches the adipose tissue lipid profiles (FIG. 2D). In light of palmitoleate's effect on improving insulin sensitivity in vitro, such a strong flux of this particular lipid from adipose tissue to muscle would have the potential to enhance insulin signaling at this site. As further support for the hypothesis that palmitoleate caused the major changes in muscle lipid metabolism in FABP$^{-/-}$ mice that contributed to improved insulin sensitivity, no significant changes in other lipid species were seen in the examination of all neutral lipids and phospholipids (FIG. 17).

Figure 18:
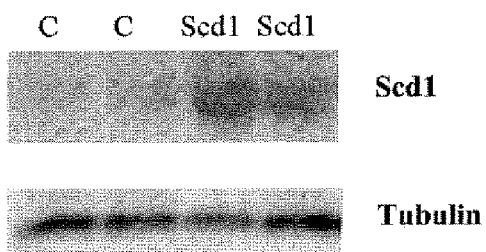
FIG. 18 is data from the adenovirus-mediated expression of SCD-1 in liver tissue of FABP$^{-/-}$ mice. FABP-deficient mice maintained on high-fat diet were injected with control (C) or SCD-1 adenoviruses. SCD-1 protein levels in liver tissues were determined with immunoblotting. Tubulin served as a loading control.

C16:1n7-palmitoleate metabolism in WT and FABP-deficient liver tissues was compared after different dietary exposures. The total palmitoleate was sharply increased by HFD in the liver tissue of WT but not FABP$^{-/-}$ mice (FIG. 4E), despite the fact that FABP-deficient mice have dramatically increased plasma palmitoleate under both conditions. This result strongly suggests that the majority of palmitoleate in liver can not be accounted for by adipose-derived FFAs and instead regulated by endogenous production by hepatocytes. Indeed, the palmitoleate level in liver is closely associated with the lipogenic gene expression at this site. Several genes of lipid synthesis pathways, particularly SCD-1, were significantly increased by high-fat diet in liver tissues of WT but not FABP$^{-/-}$ mice. Maeda et al., 2005. Thus, the high circulating palmitoleate in FABP$^{-/-}$ mice may play a regulatory role on the lipogenic programming of the liver rather than serving as substrates to drive triglyceride synthesis. If this is indeed the case, reconstitution of SCD-1 should revert this phenotype. To directly examine the role of SCD-1 in reduced lipid infiltration in liver. SCD-1 was expressed in the liver of FABP$^{-/-}$ mice on high-fat diet using adenovirus-mediated gene expression in vivo (FIG. 18). Expression of SCD-1 was sufficient to increase triglyceride synthesis in FABP-deficient mice and elevated hepatic triglyceride levels similar to that of WT mice on high-fat diet (FIG. 4F). These data demonstrated that suppression of SCD-1 activity is a key factor determining the liver steatosis phenotype in FABP-deficient mice.

Figure 5A:
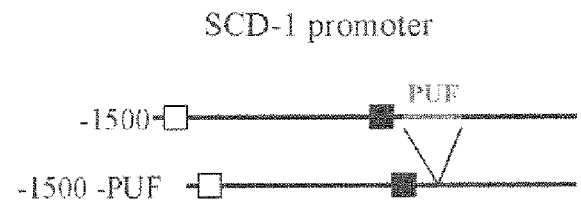
FIG. 5A-5E reflects the regulation of SCD-1 promoter activity in vivo.
Figure 5B:
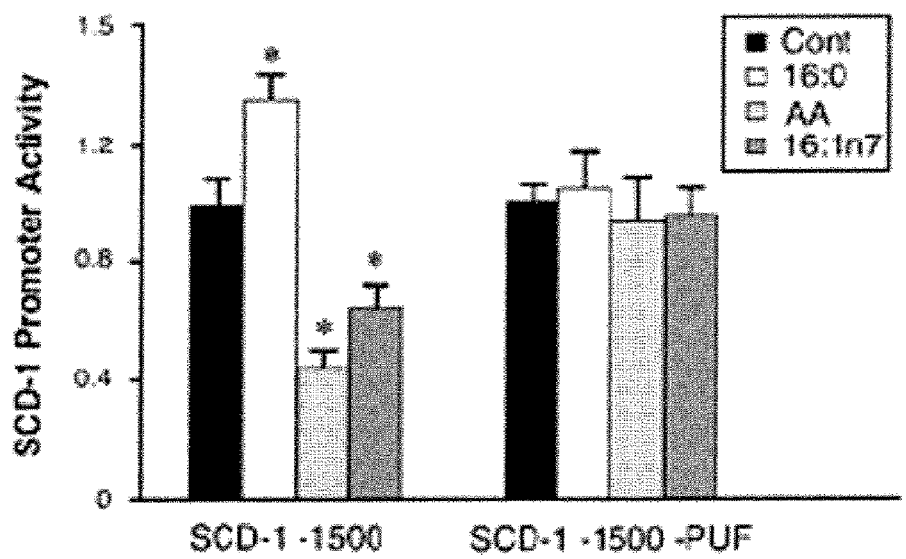
Figure 5C:
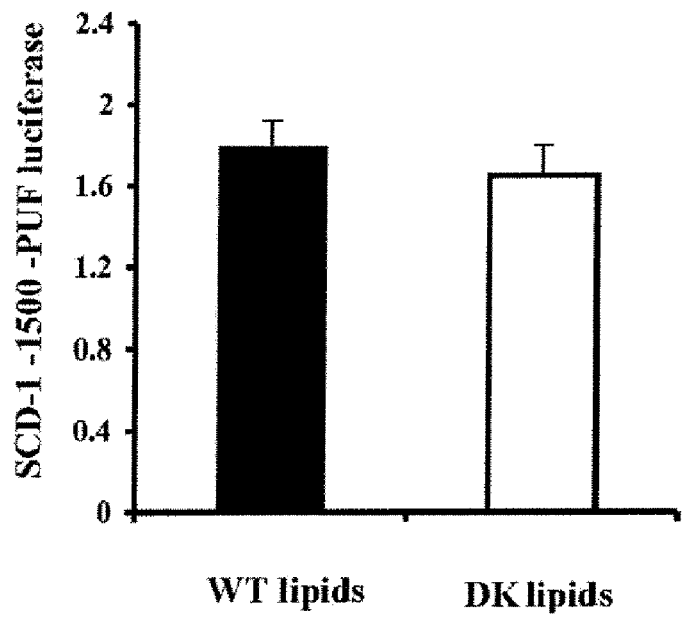
Figure 5D:
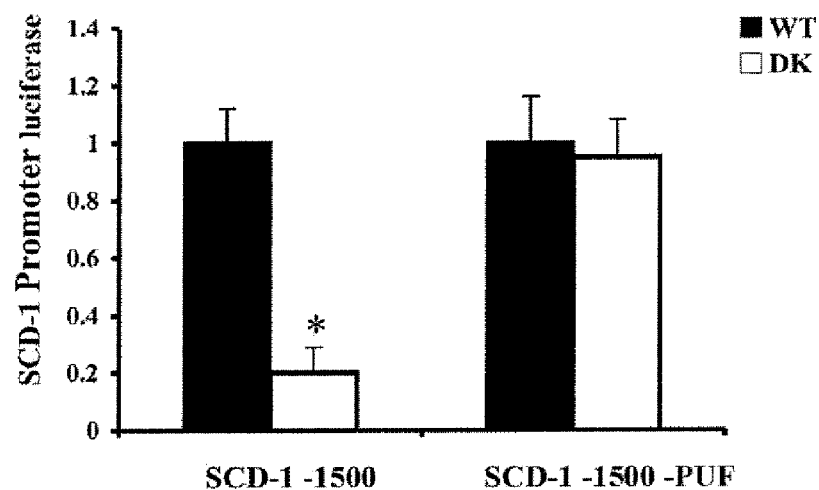

SCD-1 expression is also regulated by a lipid signal derived from adipose tissue. The link between lipid signals and FABP-deficiency induced suppression of liver SCD-1 was established using a unique SCD-1 promoter-driven reporter system that has specifically lost its responsiveness to fatty acids. A 60 bp DNA sequence has been identified in the SCD-1 promoter as a polyunsaturated fatty acid response (PUF) response element (Waters et al., 1349 (1) Biochim. Biophys. Acta. 33-42 (1997)), (FIG. 5A). This short stretch of DNA sequence is required for regulation of SCD-1 expression by PUFA but not its regulation by hormones such as insulin. Id. This PUF response element was therefore deleted from the SCD-1 promoter, and constructed in an adenoviral vector to express this reporter construct. In FAO cells infected with the intact SCD-1 promoter driven reporter, transcriptional activity was suppressed by both arachidonic acid and palmitoleate and increased by palmitate (FIG. 5B). In cells expressing the mutant promoter, however, there was no difference in the reporter activity between controls and lipid treatments (FIG. 5B), demonstrating that the PUF element is specifically required for lipid regulation of the SCD-1 promoter. Cells expressing the mutant promoter were treated with the plasma lipids extracted from WT or FABP$^{-/-}$ mice, which differentially regulate SCD-1 promoter activity (FIG. 3A). In this setting, the differential suppression of the SCD-1 promoter activity by plasma lipids of FABP$^{-/-}$ mice was lost (FIG. 5C), demonstrating that the PUF sequence is required for the SCD-1 promoter to respond to plasma-derived lipids. To test this directly in whole animals, the reporter adenoviruses were injected into WT and FABP$^{-/-}$ mice under high-fat diet. The intact SCD-1 promoter was regulated in a manner similar to liver SCD-1 mRNA in vivo. Maeda et al., 2005. Promoter reporter activity in the liver of WT mice was five-fold to ten-fold higher than that observed in FABP-deficient animals (FIG. 5D). In contrast, activity of the mutant promoter showed no difference between FABP-deficient mice and WT controls (FIG. 5D).

Figure 5E:
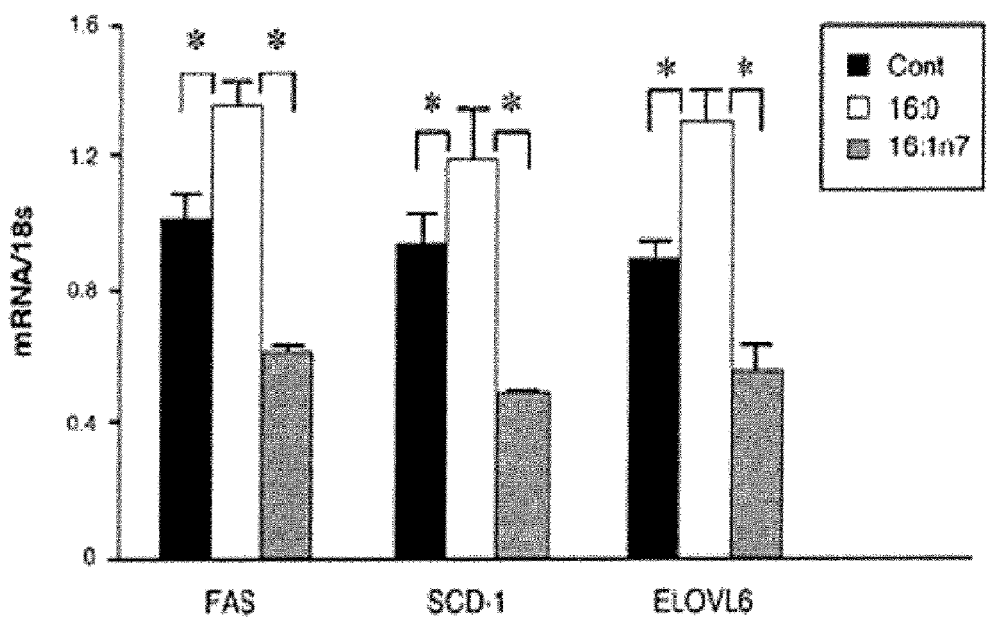

This result indicates that defective hepatic SCD-1 expression in FABP$^{-/-}$ mice is mediated by an adipose-derived plasma lipid signal, which in this case is most likely to be the high concentration of palmitoleate resulting from FABP-dependent alterations in adipose tissue lipid metabolism. Hence, the effects of lipids on liver gene expression of lipid synthesis pathway were tested. Following a 6-hour infusion as detailed in the Examples, TG-palmitoleate caused a substantial decrease in SCD-1, fatty acid synthase (FAS) and fatty acid elongase 6 (ELOVL6) expression in liver compared to vehicle-infused mice. In contrast, TG-palmitate infusion resulted in an increase in all of these lipogenic genes in liver (FIG. 5E), confirming that alteration of a single fatty acid in circulation can effectively regulate liver gene expression and palmitoleate indeed directly suppresses SCD-1 expression in this in vivo setting.

Figure 6A:
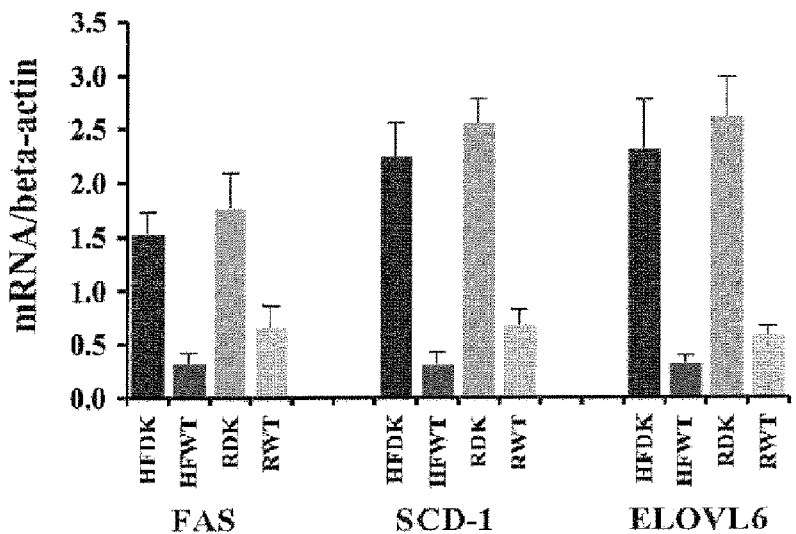
FIGS. 6A-6D present data related to the regulation of lipogenic genes in adipose and liver of WT and FABP$^{-/-}$ mice.

The present work demonstrated that adipose-specific activation of de novo lipogenesis occurs in the absence of lipid chaperones. The molecular basis of altered de novo lipogenesis in FABP$^{-/-}$ mice was investigated by examining the expression of lipogenic genes in the adipose tissues of WT and FABP$^{-/-}$ mice. These experiments revealed marked stimulation (5-fold to 10-fold) of FAS, SCD-1 and ELOVL6, the three principal enzymes that directly mediate de novo fatty acid synthesis, in adipose tissues of FABP$^{-/-}$ mice (FIG. 6A). Such an increase is quite remarkable considering that adipose tissue is already highly enriched in these enzymes. This gene expression profile is also in perfect agreement with the increased concentration of palmitoleate, the main product of de novo lipogenesis. Interestingly and unexpectedly, HFD significantly suppressed lipogenic gene expression in WT, but to a far less extent in FABP-deficient mice, which is also consistent with reduced adipose tissue and plasma palmitoleate in WT but not in FABP$^{-/-}$ mice following exposure to HFD. Several recent reports have demonstrated that both humans and rodents with obesity and diabetes exhibit reduction in lipogenic gene expression in adipose tissue. Dubois et al., 2006; Moraes et al., 2003; Nadler et al., 2000. Such changes would most likely result in decreased adipose tissue palmitoleate and a less favorable plasma lipid profile, considering the effects of palmitoleate on liver and muscle metabolism described herein.

Figure 6B:
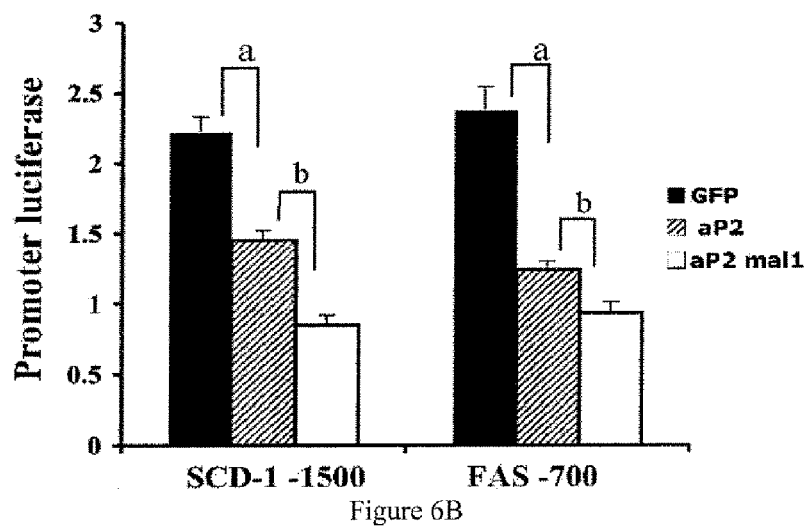
Figure 6C:
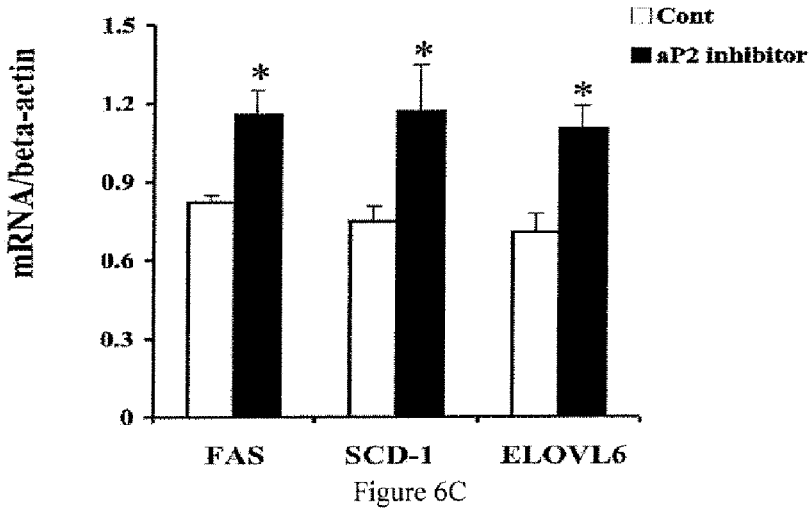
Figure 19:
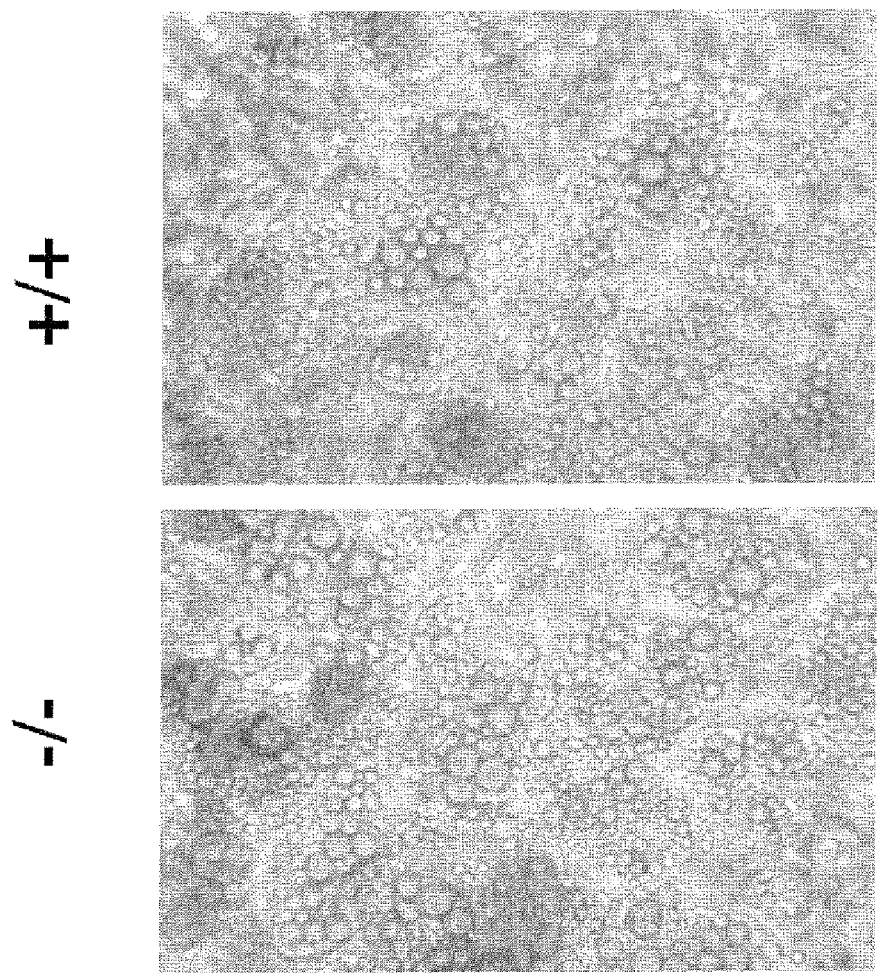
FIG. 19 shows images of differentiated WT and FABP-deficient adipocytes. Pre-adipocyte cell lines were derived from WT (+/+) or FABP-deficient (−/−) mice as described in the Examples and differentiated into mature adipocytes. Cells were fixed and stained with Oil-red-O.

The marked increase of genes in fatty acid synthesis in adipose tissue of FABP mice and the unresponsiveness to high-fat diet suggests that these lipid chaperones are integral components of lipid-mediated regulation of gene expression. To directly address this, adipogenic cell lines from FABP-/- mice were differentiated them into adipocytes (FIG. 19). In this system, exogenously expressed FABPs strongly and additively suppressed both SCD-1 and FAS promoter activities (FIG. 6B). These results indicate that lipid chaperones suppress the expression of lipogenic genes in adipocytes and loss of these proteins leads to increased expression of genes involved in lipid synthesis. This observation agrees with that observed in adipose tissue of FABP-deficient mice. This pattern was tested in vivo in an alternative experimental system where aP2 function in mice is blocked through an orally administered synthetic inhibitor. This treatment has been demonstrated to generate effects that closely paralleled the beneficial phenotypes of genetic FABP-deficiency in terms of insulin sensitivity and atherosclerosis. Furuhashi et al., 2007. Such inhibition would be expected to increase lipogenic gene expression if aP2 acts as a suppressor of these genes, and indeed, treatment of mice with aP2 inhibitor increased lipogenic gene expression in adipose tissues of WT mice (FIG. 6C).

Figure 6D:
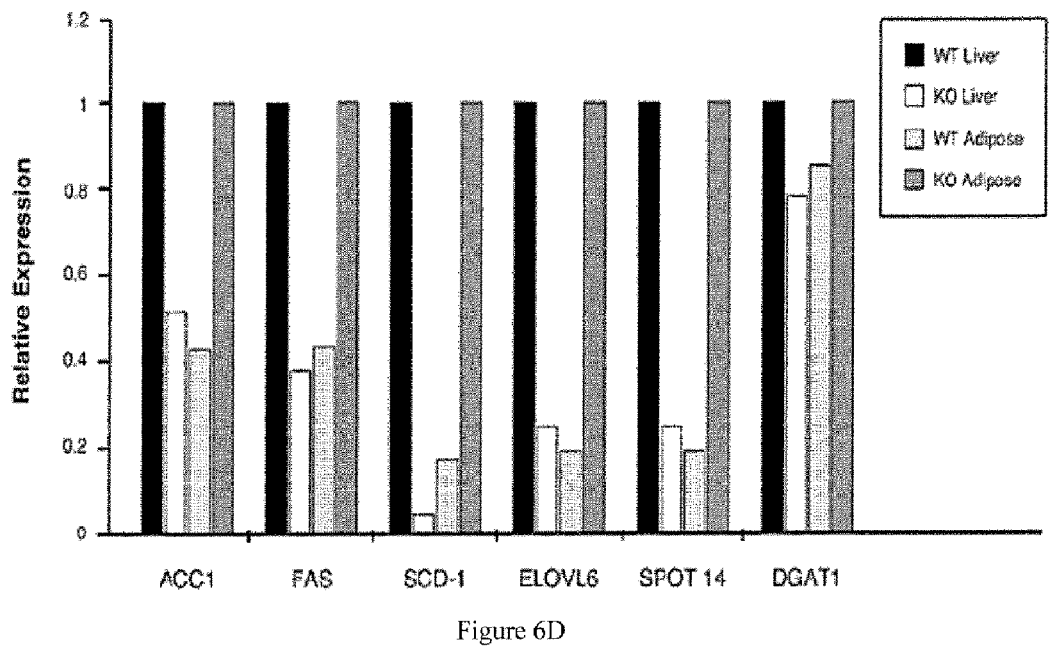

The work presented herein has identified an opposite pattern of SCD-1 expression in liver of FABP-deficient mice as compared to adipose tissue, a pattern likely to be generated by the product of this enzyme, C16:1n7-palmitoleate. This pattern may apply to broader array of genes involved in lipogenesis in these tissues. Therefore, the major genes in fatty acid, cholesterol and triglyceride synthesis were examined, revealing that these genes formed a striking and diametrically opposite pattern of expression between adipose and liver tissues of FABP$^{-/-}$ mice (FIG. 6D).

Figure 7A:
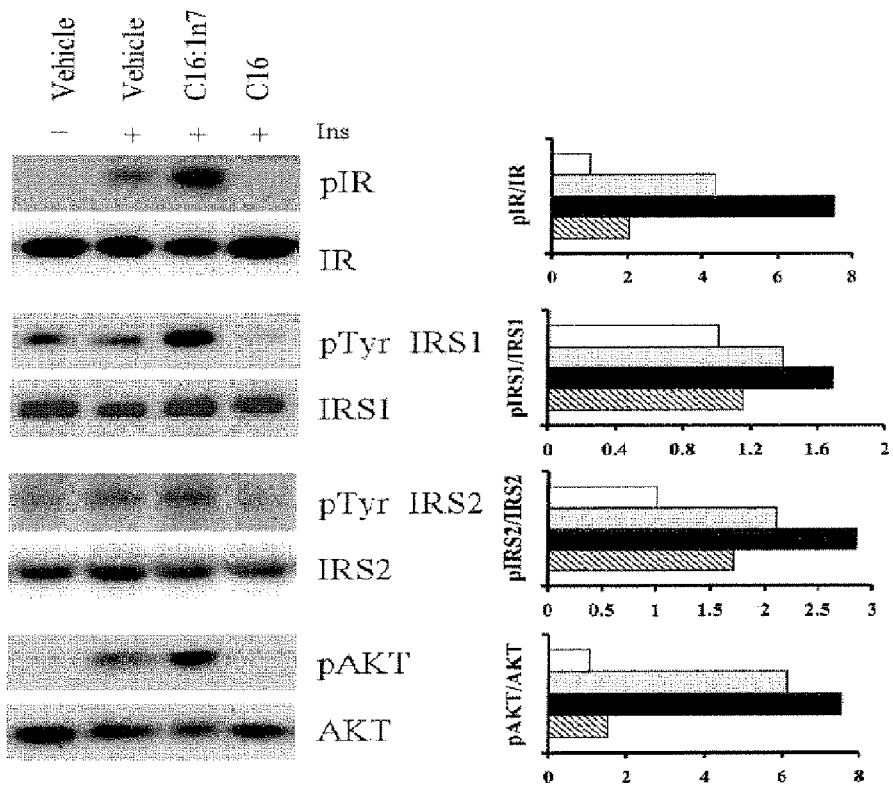
FIGS. 7A-7G show data on the regulation of insulin signaling and glucose metabolism by palmitoleate.
Figure 7B:
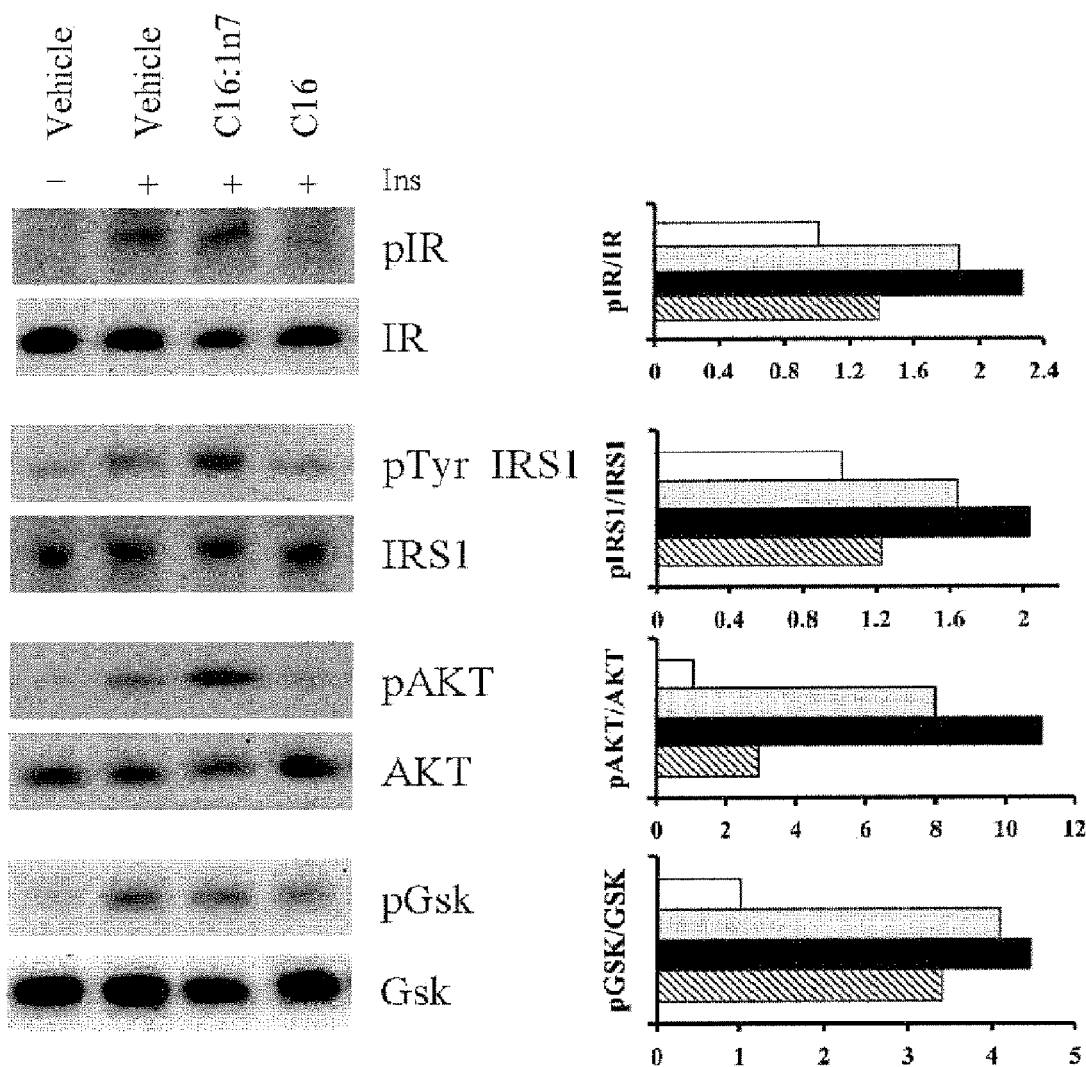
Figure 20:
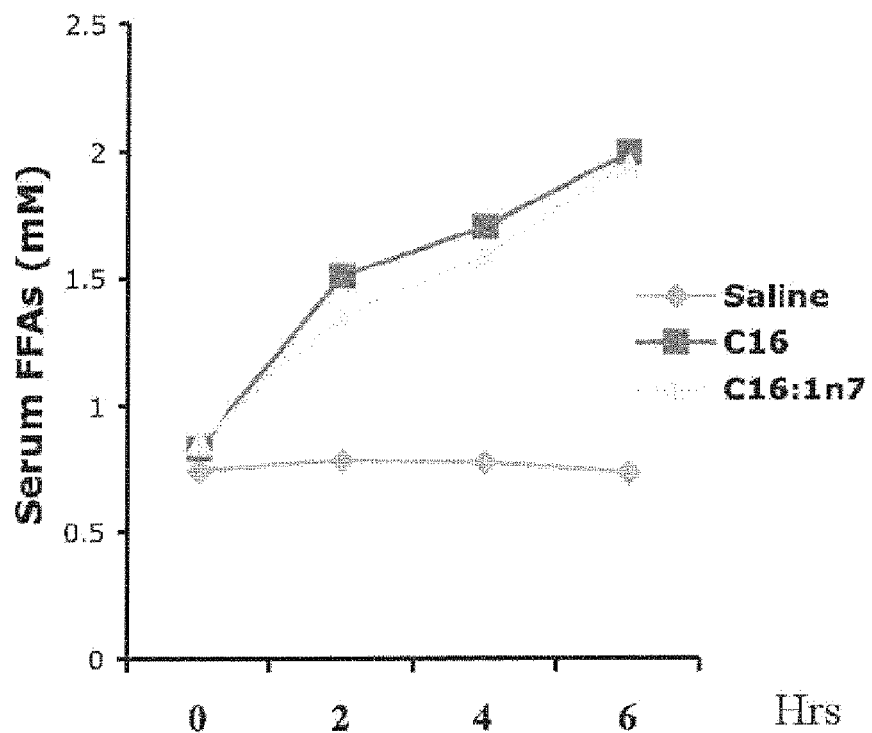
FIG. 20 reflects the plasma fatty acid levels during lipid-infusion. Blood samples were collected by tail bleeding from mice that were infused with either TG-palmitate (C16) or TG-palmitoleate (C16:1n7) and plasma free fatty acid was determined with a fatty acid assay kit as described in the Examples.

The present invention also provides for the regulation of insulin action by increased circulating palmitoleate. To study whether palmitoleate regulates systemic metabolic responses, lipid infusions were administered in conscious mice. Lipid infusion has been used widely to investigate the relationship between plasma FFAs and insulin resistance, but almost all studies using this protocol utilized preparations of natural lipid products containing a variety of fatty acids. Kim et al., 114 J. Clin. Invest. 823-27 (2004); Kim et al., 277 J. Biol. Chem. 32915-22 (2002); Yu et al., 277 J. Biol. Chem. 50230-36 (2002). To define the effects of individual fatty acids on metabolic regulation, INTRALIPID® fat emulsion infusions (Kabivitrum, Inc., CA) with triglycerides composed of a single fatty acid, either TG-palmitoleate or TG-palmitate, were prepared. Infusion of either lipid resulted in a 2-fold increase in total plasma FFA levels with similar dynamics (FIG. 20). Although TG-palmitate suppressed the entire proximal insulin-signaling pathway including activation of insulin receptor and phosphorylation of insulin receptor substrate 1, 2 and AKT in liver as compared to vehicle controls, TG-palmitoleate strongly potentiated each of these insulin actions (FIG. 7A). Similar effects of both lipids on muscle tissue were observed. In contrast, palmitoleate enhanced and palmitate impaired insulin receptor signaling (FIG. 7B). These results clearly indicate that specific alteration of a single serum lipid, C16:1n7-palmitoleate, is sufficient to regulate insulin actions in peripheral tissues, and that increased circulating palmitoleate enhances insulin sensitivity.

Figure 7C:
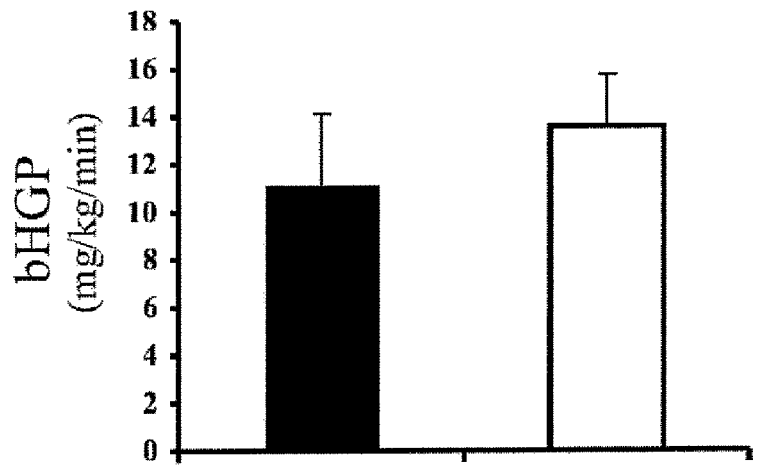
Figure 7D:
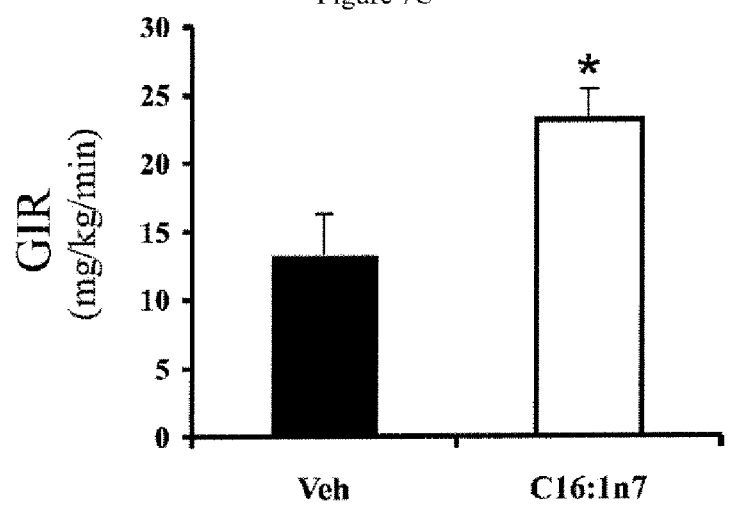
Figure 7E:
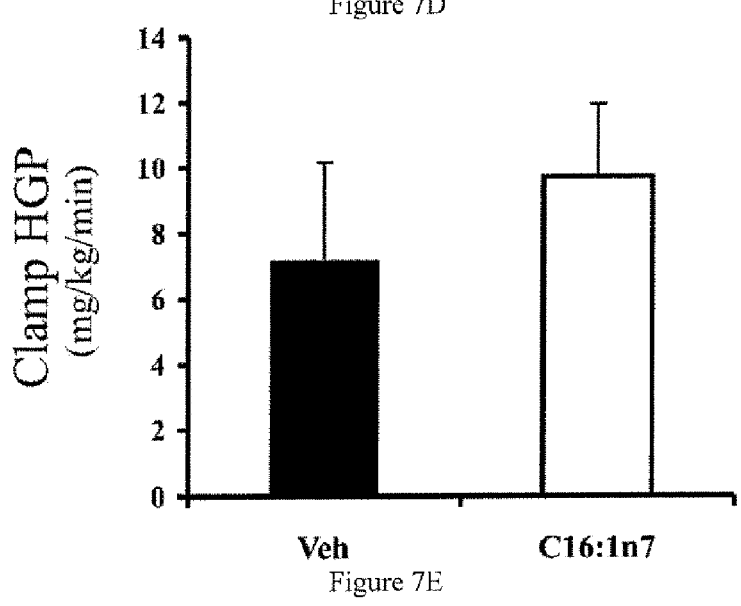
Figure 7F:
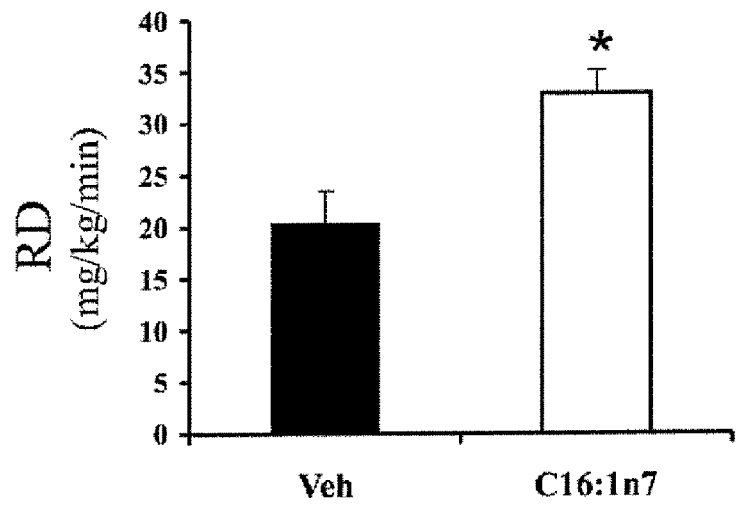
Figure 7G:
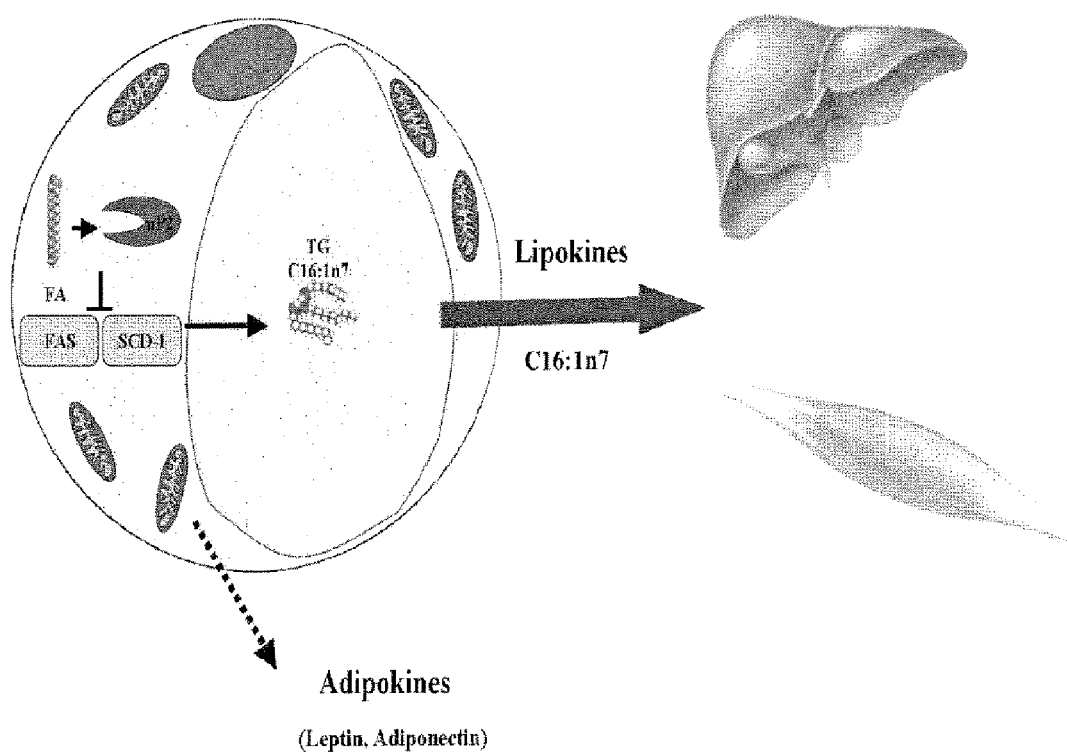
Figure 21:
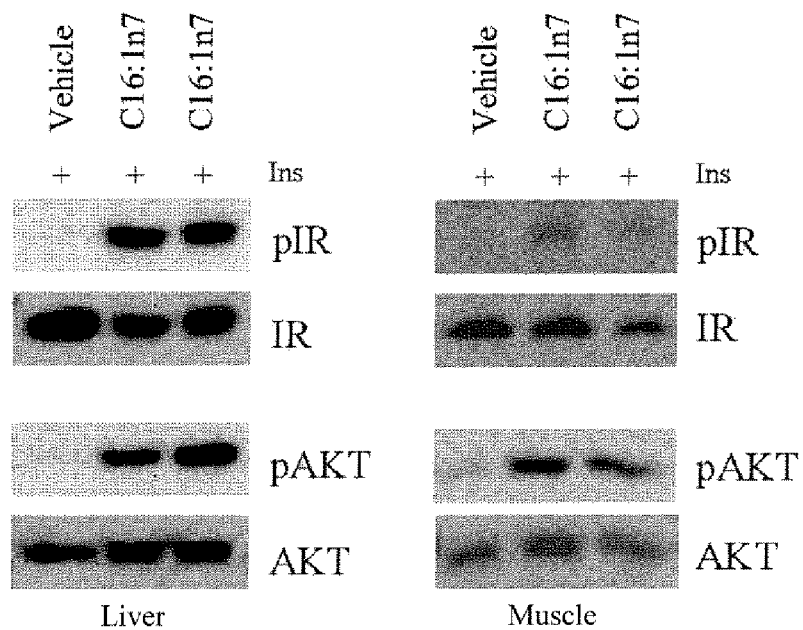
FIG. 21 shows insulin signaling in mice infused with vehicle or palmitoleate. The left panel presents the insulin-stimulated phosphorylation of insulin receptor and AKT in liver of mice infused with vehicle or palmitoleate. The right panel shows insulin-stimulated phosphorylation of insulin receptor and AKT in muscle of mice infused with vehicle or palmitoleate. Mice were infused with vehicle or palmitoleate at 3.3 µl/min for six hrs, and insulin (1 U/Kg) was injected through the infusing tubing. Three minutes after insulin injection, tissues were collected and immunoblotting analyses were performed.

To investigate whether the increased insulin signaling by elevated serum palmitoleate can be translated into improved glucose metabolism, hyperinsulinemic-euglycemic clamp studies were performed on mice infused with either vehicle or palmitoleate. To enable delivery of lipid at a rate that is compatible with clamp studies, fatty acid:palmitoleate was used instead of TG:palmitoleate. That palmitoleate enhanced both muscle and liver insulin signaling in this setting was confirmed by examining insulin stimulated activation of insulin receptor and AKT (FIG. 21). Hyperinsulinemic-euglycemic clamp studies indicated that mice infused with palmitoleate required significantly higher glucose infusion rate to maintain euglycemia (FIG. 7D). Neither basal nor clamped hepatic glucose production was significantly changed by palmitoleate infusion as compared to vehicle controls (FIGS. 7C and 7E). Instead, the increased glucose infusion rate in these mice was driven by enhanced whole body glucose metabolism (FIG. 7F), confirming that the increased insulin signaling by palmitoleate infusion can be directly reflected as improved glycemic control in conscious mice. This observation indicates that, indeed, C16:1n7-palmitoleate acts as an insulin-sensitizing hormone that improves glucose metabolism.

EXAMPLES

Animals

Mice with homozygous null mutations in aP2 and mal1 (aP2-mal1$^{-/-}$, FABP$^{-/-}$) have been backcrossed more than twelve generations into C57BL/6J genetic background as previously described. Maeda et al., 2005. Mice were maintained on regular chow diet (RD) or placed on high-fat diet (HFD) at four-weeks-of-age for 16 weeks to induce dietary obesity. The Institutional Animal Care and Use Committee (Harvard School of Public Health) approved all studies. Mice on HFD diet were administered with aP2 inhibitor daily via oral gavage at a dose of 40 mg/kg/day for two months. Adipose tissues were collected at the end of the treatment for gene expression analyses.

Quantitative Lipid Profiling

The lipids from plasma and tissues were extracted in the presence of authentic internal standards by published methods (Folch et al., 1957), using chloroform:methanol (2:1 v/v). Individual lipid classes within each extract were separated by liquid chromatography (Agilent Technologies model 1100 Series). Each lipid class was trans-esterified in 1% sulfuric acid in methanol in a sealed vial under a nitrogen atmosphere at 100° C. for 45 min. The resulting fatty acid methyl esters were extracted from the mixture with hexane containing 0.05% butylated hydroxytoluene and prepared for gas chromatography by sealing the hexane extracts under nitrogen. Fatty acid methyl esters were separated and quantified by capillary gas chromatography (Agilent Tech. model 6890) equipped with a 30 m DB-88MS capillary column (Agilent Tech.) and a flame-ionization detector.

An automated analysis of fatty acid methyl esters using a XYZ robotic autosampler has been described (de Koning et al., 922 J. Chromatogr. A 391 (2001). After preparing manually a solution of fatty acids, the autosampler is used to add reagent (sodium methylate), agitate, and finally inject into the gas chromatograph. That procedure takes about 15 min before analysis of the samples.

Additionally, a simple and rapid method for determination of short-chain fatty acids by HPLC with ultraviolet detection has been reported (Stein et al., 576 J. Chromatogr. 53 (1992)). A simple HPLC system allowing the separation of short, medium, and long chain fatty acids has been described (Kroumova et al., 225 Anal. Biochem. 270 (1995)). A sophisticated and precise method combining HPLC and mass spectrometry was developed to measure short-chain fatty acids in blood (Van Eijk et al., 877 J. Chromatogr. B 719 (2009)). Positional and conformational isomers are more easily separated by HPLC than GLC. All kinds of detectors may be used but separations of derivatized fatty acids are usually monitored with UV spectrophotometer or by fluorimetry.

Efficient purification and analysis procedures of polyunsaturated methyl esters have been described using reversed-phase HPLC and light-scattering detection (Mansour, 1097 J. Chromatogr. A 54 (2005)). A similar method has also been developed for the separation and quantitative analysis of fatty acid methyl esters in three vegetal oils, response factors being accurately determined (Bravi et al., 1134 J. Chromatogr. A 210 (2006)). A pertinent overview of the application of reversed-phase HPLC for the separation of polyunsaturated fatty acids may be found in Rao et al., 33 J. Chromatogr. Sci. 9-21 (1995). A sensitive fluorescence method for the direct determination of free fatty acids has been proposed using the reagent DBD-PZ (Tokyo Chem. Indus. Co, Prod. No A5555; Ueno et al., 47 Chem. Pharm. Bull. 1375 (1999)).

Thus, for example, in detecting the C16:1n7-palmitoleate in a subject's serum, according to standard techniques, body mass index (BMI; in kg/m$^2$) is calculated. The subject may be categorized normal-weight, overweight, and obese, respectively. Optionally, human subjects may asked a set of questions about their overall health, diet, and smoking habits. Blood is drawn from the subject, optionally across a range of fasting and postprandial states, from an antecubital vein into vacuum evacuated tubes with no anticoagulant. The tubes are centrifuged and the serum was aliquoted into cryovials for storage at −80° C. Serum total and HDL-cholesterol concentrations are measured by standard techniques. Lipids are extracted from 400 µL of serum, an internal standard may be added before extraction. The serum lipids are separated by using thin-layer chromatography with a solvent system of hexane/diethyl ether/acetate (85:15:1 by volume). The lipid bands are visualized under ultraviolet light after the plates were sprayed with a solution of 0.1% (wt:vol) 8-anilio-1-napthalene sulfonic acid. Serum cholesterol ester, triacylglycerol, and phospholipid bands are scraped into glass test tubes and methylated in 6% sulfuric acid in methanol for 2 hr (for cholesterol esters and triacylglycerols) or 12-16 hr (phospholipids). The samples are then eluted into hexane and stored at −20° C. The fatty acid methyl esters may be analyzed by using a DB-225 column installed on an HP 6890 Series Gas Chromatograph (Agilent, Palo Alto, Calif.) with flame ionization detection. Blank samples are extracted, separated, and analyzed, and the peak areas subtracted from the corresponding areas of the sample runs after adjustment for internal standard recovery had been made.

Adenovirus Production and Infection of Adipocytes and Mouse

Adenovirus were constructed by cloning aP2, mal1, and SCD-1 cDNAs into adenoviral vector pAD/CMV/V5-DEST, and viruses were produced as described in VIRAPOWER™ Adenoviral Expression System (Invitrogen Corp., Carlsbad, Calif.). SCD-1 (−1500 bp) or FAS (−700 bp) promoters were amplified from mouse genomic DNA with PCR and cloned upstream of Firefly luciferase gene in vector pGL3 (Promega Corp., Madison, Wis.). The mutant SCD-1 promoter was produced by inserting two partial fragments of the −1500 bp promoter lacking the 60 bp PUF element in front of luciferase gene in vector pGL3. The entire reporter cassettes were subcloned into vector pAD/PL-DEST (Invitrogen) to produce adenoviruses. Five (5) μl crude virus were used to infect differentiated adipocytes in 96-well plate for reporter assays. Adenovirus used to infect mice were purified with CsCl ultracentrifugation and de-salted with a PD 10 column. Adenovirus were tittered and administrated via tail vein injection ($10^{11}$ viral particles per mouse).

Plasma Lipid Extraction, Lipid Treatments, Immunoprecipitation and Immunoblotting Samples of 200 μl serum were collected using heparin-coated glass tubes and spun at 13,000 g in a microcentrifuge to separate the plasma. Plasma lipids were extracted by adding 0.3 ml 0.5 M $KH_2PO_4$, 1.5 ml chloroform, and 0.5 ml methanol. After vortexing 2 min and centrifugation in a microcentrifuge, the lower phase was collected with a Pasteur pipette through the protein disk and evaporated. Lipids were dissolved in 50 μl DMEM with 2% fatty acid-free BSA. Two (2) μl of either whole plasma or plasma lipids were used to treat cells in 96-well plates. Tissue protein lysates was separated with SDS-PAGE gels and phosphorylated or total proteins were detected with the following antibodies: phospho AKT Serine 473, AKT, insulin receptor, phospho-tyrosine (Santa Cruz Biotech.); IRS-1 and IRS-2 (Upstate); phospho-GSK and GSK (Cell Signaling Tech.); phospho-insulin receptor from (Calbiocbem). To immunoprecipitate IRS-1 and IRS-2, 1000 μg tissue protein lysate was incubated with 3 μl anti-IRS-1 or anti-IRS-2 antibodies and 40 μl Protein A beads (Amersham) overnight. Proteins bound to beads were eluted with SDS loading buffer.

Lipid Infusion and Hyperinsulinemic-Euglycemic Clamp

INTRALIPID® fatty acid lipid infusion solution with 2 mM triglycerides:palmitate or palmitoleate were prepared using a previously described protocol with modifications (Stein et al., 1997). Briefly, lipids were dissolved in a solvent containing 5% glycerol and 0.72% phosphocholine in 0.9% saline, heated at 80° C. for 10 min, and then sonicated 1 min four times. For TG:palmitoleate, the heating was omitted to avoid oxidization of the lipids. Lipids stay in suspension for a week, so to prevent clogging the preparations must be vortexed well before loading the syringe and tubing. Seven days before lipid infusion, mice were anesthetized and an indwelling catheter inserted in the left internal jugular vein, then the animals were left to recover the following days. After overnight fasting, lipids were infused at a rate of 500 μl/kg/min for six hours. At the end of the infusion, insulin (1 U/Kg) was injected into mice via the infusion tubing and tissues were collected for subsequent gene expression and immunoblotting analyses. To determine serum FFA level during lipid infusion, blood was collected from mouse tails at different time intervals and spun down to collect plasma. Serum FFAs were determined using a commercial kit (Wako Chem.). TG:palmitate and TG:palmitoleate are difficult to dissolve at a concentration that are compatible with the infusion rate of hyperinsulinemic-euglycemic clamp study and yet maintain efficient delivery of these lipids. Therefore fatty acid: palmitoleate was used to infuse mice for clamp study. Palmitoleate was dissolved in saline containing 2% BSA (vehicle) at 15 mM with repeated sonications and was infused through the tubing at a rate of 3.3 μl/min for two hours. A standard hyperinsulinemic-euglycernic clamp was then performed as previously described (Furuhashi et al., 2007). Vehicle or palmitoleate solution was used to dissolve tracer $^3$H-glucose and so lipid was also infused at 3.3 μl/min throughout the 4-hour period of clamp study.

C16:1n7 is also available commercially from, for example Gallade Chemical, Inc. (Santa Ana, Calif.) and Sigma-Aldrich® chemicals (St. Louis, Mo.). Natural sources of C16:1n7 include macadamia nuts and Sea-Buckthorn (*Hippophae* L.).

We claim:

1. A method of improving glycemic control/glucose metabolism in a subject in need thereof, comprising the step of administering a pharmaceutical composition or nutraceutical comprising at least 75% w/v C16:1 n7-palmitoleate; wherein said administering of C16:1 n7-palmitoleate is repeated or continued until a serum concentration ranging from about 12.5 μM to about 17.5 μM C16:1 n7-palmitoleate is achieved, and wherein the administration of C16:1 n7-palmitoleate has at least one of the following activities: reduces the impact of lipid-enriched diet on lipid metabolism and lipid composition; improves insulin sensitivity; enhances insulin signaling in muscle tissue; regulates insulin actions in peripheral tissues; rescues diet-induced reduction in insulin-stimulated AKT phosphorylation; potentiates the proximal insulin-signaling pathway, wherein said potentiation is one of activation of insulin receptor, or phosphorylation of insulin receptor substrate 1, 2 protein kinase AKT in liver; decreases the expression of lipogenic genes in liver, including SCD-1, fatty acid synthase (FAS), and/or fatty acid elongase 6 (ELOVL6).

* * * * *

UNITED STATES PATENT AND TRADEMARK OFFICE
CERTIFICATE OF CORRECTION

PATENT NO. : 9,239,334 B2  
APPLICATION NO. : 13/062527  
DATED : January 19, 2016  
INVENTOR(S) : Cao et al.

Page 1 of 1

It is certified that error appears in the above-identified patent and that said Letters Patent is hereby corrected as shown below:

In the Specification

At Column 1, Lines 5-11:
"FEDERAL FUNDING
This invention was made with U.S. government support under grants DK71507-04 and DK064360, each awarded by the National Institutes of Health. The U.S. government has certain rights in the invention."

Should be replaced with:
— GOVERNMENT SUPPORT
This invention was made with government support under DK071507 and DK064360 awarded by the National Institutes of Health. The government has certain rights in the invention. —

Signed and Sealed this  
Twelfth Day of May, 2020

Andrei Iancu  
*Director of the United States Patent and Trademark Office*